(12) United States Patent
Leunbach et al.

(10) Patent No.: US 6,256,527 B1
(45) Date of Patent: *Jul. 3, 2001

(54) METHOD FOR DETERMINING OXYGEN CONCENTRATION

(75) Inventors: Ib Leunbach, Dragør; Jan Henrik Ardenkjaer-Larsen, Vanløse, both of (DK)

(73) Assignee: Nycomed Imaging AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/027,560

(22) Filed: Feb. 23, 1998

Related U.S. Application Data

(62) Division of application No. 08/546,146, filed on Oct. 20, 1995, now Pat. No. 5,765,562.

(30) Foreign Application Priority Data

Sep. 8, 1995 (GB) .................................................. 9518442

(51) Int. Cl.[7] ...................................................... A61B 5/055
(52) U.S. Cl. ............................. 600/420; 324/309; 424/9.3
(58) Field of Search .................................... 600/420, 309; 324/307, 309, 316; 424/1.65, 9.3

(56) References Cited

U.S. PATENT DOCUMENTS

| | | | |
|---|---|---|---|
| 4,984,573 | * | 1/1991 | Leubach .............................. 128/653 |
| 5,289,125 | * | 2/1994 | Ehnholm .............................. 324/309 |
| 5,494,030 | * | 2/1996 | Swartz et al. ........................ 128/632 |
| 5,765,562 | * | 6/1998 | Leunbach et al. ................ 128/653.4 |

* cited by examiner

Primary Examiner—Marvin M. Lateef
Assistant Examiner—Eleni Mantis Mercader
(74) Attorney, Agent, or Firm—Bacon & Thomas

(57) ABSTRACT

A method for determining the oxygen concentration of a sample using electron spin resonance enhanced magnetic resonance imaging.

24 Claims, 9 Drawing Sheets

Perdeuterated trityl in ◆ water and ■ plasma at 37°C. Linewidth as a function of oxygen concentration measured at X-band.

Non-deuterated hydroxy trityl in ◆ water and ■ plasma at 37°C. Linewidth as a function of oxygen concentration measured at X-band.

Deuterated hydroxy trityl in water at 37°C. ◆ Envelope and ■ Lorentzian linewidth and • $2(\sqrt{3}\gamma_e T_{1e})^{-1}$ Deuterated hydroxy trityl in water at 23°C. ◆ Envelope and ■ Lorentzian linewidth and • $2(\sqrt{3}\gamma_e T_{1e})^{-1}$ Deuterated hydroxy trityl in blood at 23°C. ◆ Envelope and ■ Lorentzian linewidth and ● $2(\sqrt{3}\gamma_e T_{1e})^{-1}$ $(\gamma_e T_{1e} T_{2e})^{-1}$ or the $B_1$ of half maximum DNP enhancement in mG. Deuterated hydroxy trityl in ■ water and ● blood at 37°C and ◆ water at 23°C

METHOD FOR DETERMINING OXYGEN CONCENTRATION

This application is a Division of nonprovisional application Ser. No. 08/546,146 filed Oct. 20, 1995 and currently U.S. Pat. No. 5,765,562.

FIELD OF THE INVENTION

This invention relates to a method for determining the oxygen concentration of a sample, for example a human or animal body, more particularly to the use of electron spin resonance enhanced magnetic resonance imaging (OMRI) of a sample to determine its oxygen concentration, and especially to the use of OMRI for the generation of images indicative of dissolved oxygen concentration in a sample.

BACKGROUND OF THE INVENTION

Oxygen plays a key role in the metabolic processes of biological systems and many conditions may be linked to abnormal levels of oxygen in the body. To provide a better understanding of this metabolic role and to aid clinical diagnosis, there is clearly a need to improve the means by which the level of oxygen in bodily tissues may be measured.

Conventional methods for determining oxygen concentrations are unsatisfactory. One such technique involves inserting a Clark electrode directly into a blood vessel to determine the local oxygen concentration. Clearly such a technique is of limited scope being invasive and usable only locally.

Non-invasive techniques have been slow to develop and generally are not suited to the study of tissues lying deep beneath the surface of a sample.

The most well-developed and accurate method for use ex vivo is that of "spin-label oximetry" in which changes in the esr linewidth of a free radical caused by the presence of oxygen are monitored. Such techniques generally use solid phase immobilized paramagnetic species as the spin-label and thus are not suited for in vivo measurements.

Electron spin resonance enhanced MRI, referred to herein as OMRI(Overhauser MRI) but also referred to in earlier publications as ESREMRI or PEDRI, is a well-established form of MRI in which enhancement of the magnetic resonance signals from which the images are generated is achieved by virtue of the dynamic nuclear polarization (the Overhauser effect) that occurs on VHF stimulation of an esr transition in a paramagnetic material, generally a persistent free radical, in the subject under study. Magnetic resonance signal enhancement may be by a factor of a hundred or more thus allowing OMRI images to be generated rapidly and with relatively low primary magnetic fields.

OMRI techniques have been described by several authors, notably Leunbach, Lurie, Ettinger, Grücker, Ehnholm and Sepponen, for example in EP-A-296833, EP-A-361551, WO-A-90/13047, J. Mag. Reson. 76:366–370(1988), EP-A-302742, SMRM 9:619(1990), SMRM 6:24(1987), SMRM 7:1094(1988), SMRM 8:329(1989), U.S. Pat. No. 4,719,425, SMRM 8:816(1989), Mag. Reson. Med. 14:140–147 (1990), SMRM 9:617(1990), SMRM 9:612(1990), SMRM 9:121(1990), GB-A-2227095, DE-A-4042212 and GB-A-2220269.

In the basic OMRI technique, the imaging sequence involves initially irradiating a subject placed in a uniform magnetic field (the primary field $B_o$) with radiation, usually VHF radiation, of a frequency selected to excite a narrow linewidth esr transition in a paramagnetic enhancement agent which is in or has been administered to the subject. Dynamic nuclear polarization results in an increase in the population difference between the excited and ground nuclear spin states of the imaging nuclei, i.e. those nuclei, generally protons, which are responsible for the magnetic resonance signals. Since MR signal intensity is proportional to this population difference, the subsequent stages of each imaging sequence, performed essentially as in conventional MRI techniques, result in larger amplitude MR signals being detected.

In any OMRI experiment under ambient conditions, paramagnetic oxygen will have a finite effect on the spin system present. Generally speaking, this may be dismissed as a secondary effect when compared to the primary interaction of the radical electron spin and the nuclear spin system. Nonetheless, it has been proposed that this effect may be used to determine oxygen concentration within a sample. However such research has concentrated particularly on the use of nitroxide spin labels; radicals which suffer the inherent disadvantage of having broad linewidth esr resonances and therefore low sensitivity to the effects of oxygen. Thus, to date, the effect of oxygen has been recognised only in a qualitative sense and any attempt to attach a quantitative significance to the oxygen effect has failed.

For example, Grücker et al (MRM, 34:219–225(1995)) reported a method for calculating oxygen concentration by measuring the Overhauser effect in a nitroxide radical and relating the non-linear effect of oxygen on the Overhauser Factor to its concentration. This involved taking two images, one on-resonance and one off-resonance, and using a first order approximation to arrive at the oxygen concentration. However, Grücker observed that the correlation between actual and calculated oxygen concentration was poor and therefore that the method was inherently inaccurate. This was attributed to the large number of parameters involved in the calculation.

Ehnholm (U.S. Pat. No. 5,289,125) has proposed an OMRI technique in which signals from a paramagnetic material are detected under at least two different sets of operating parameters whereby to generate images of various physical, chemical or biological parameters. While oxygen tension was one of several such parameters, Ehnholm did not demonstrate the use of the technique to quantitate dissolved oxygen.

SUMMARY OF THE INVENTION

The present invention relates to a non-invasive method for determining the oxygen concentration of a sample. It involves manipulation of the Overhauser effect in which polarisation is dynamically transferred to protons when an electron spin resonance transition of an administered persistent free radical is saturated. More specifically, the method is based on observing and manipulating the varying enhancement of a proton signal due to the changed saturation characteristics of a free radical in the presence of oxygen.

Thus viewed from one aspect the present invention provides a method of determining oxygen concentration in a sample, for example a human or non-human, preferably mammalian, subject, said method comprising the following steps: introducing into said sample an effective amount of a physiologically tolerable free radical (generally a persistent radical) having an esr transition with a linewidth (measured in water at 37° C.) of less than 400 mG, preferably less than 150 mG; irradiating said sample with radiation (generally referred to herein as VHF radiation) of an amplitude (i.e. power) and frequency selected to stimulate an electron spin resonance transition of said radical; detecting electron spin resonance enhanced magnetic resonance signals from said sample under at least first, second and third conditions, whereby under said first and second conditions said radiation is of a first frequency, under said third conditions said radiation is of a second frequency different from said first frequency, under said first, second and third conditions said radiation is of a first, second and third amplitude, said first and second amplitudes at least being different from each other; and manipulating said detected signals whereby to determine oxygen concentration in said sample.

DETAILED DESCRIPTION OF THE PREFERRED EMBODIMENTS

Figure 1:
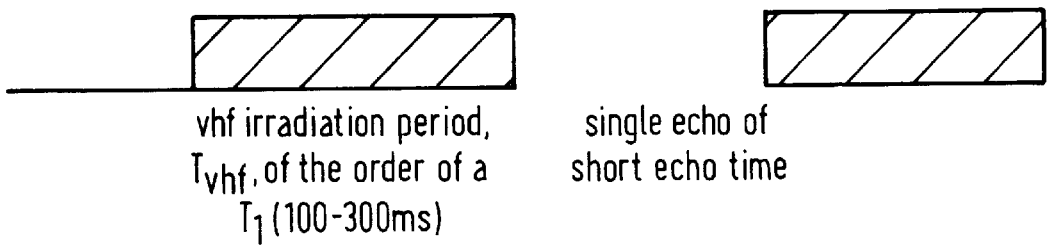
FIG. 1 is a schematic example of an OMRI sequence used in the method of the invention.

In a preferred embodiment, the method of the invention comprises:

(a) introducing the radical, e.g. parenterally, for example by injection into body tissue or into the vasculature;

(b) generating a first OMRI image of said sample at VHF power $P_A$, irradiation period $T_{VHF1}$ and on-resonance ($\Delta H=0$) (i.e. where the frequency of the radiation is selected to be the resonance frequency of the esr transition);

(c) generating a second OMRI image of said sample at a second VHF power $P_B$, irradiation time $T_{VHF1}$ and on-resonance ($\Delta H=0$);

(d) generating a third OMRI image of said sample at VHF power $P_C$ (eg equal to $P_A$ or $P_B$), irradiation time $T_{VHF1}$ and off-resonance ($\Delta H \neq 0$, for example 100–200 mG);

(e) manipulating the images obtained in steps (b) to (d) and calibrating using parameters determined ex vivo to provide an oxygen image of said sample.

In an especially preferred embodiment, a fourth and fifth OMRI image are additionally generated in the imaging sequence. The conditions for the fourth image are identical to the first image but the VHF irradiation time $T_{VHF2}$ is different (for example twice as long, i.e. $T_{VHF2}=2T_{VHF1}$) and the fifth image is obtained without VHF irradiation, e.g. is a native image of intensity $I_o$, generated by conventional MRI with a repetition time $T_R=T_{VHF}$.

In a further embodiment, a native image (i.e. one obtained by conventional MRI) of the sample (e.g. body) may be generated to provide structural (e.g. anatomical) information upon which the oxygen image may be superimposed. In this way, precise location of for example an oxygen deficient tumour will be possible.

Accurate measurement of the level of oxygen in bodily tissues is an invaluable aid to the clinician and the method of the invention has a variety of end uses. For example, knowledge of the concentration of oxygen dissolved in blood can be used (through known rate constants) to calculate the concentration of oxygen associated with haemoglobin. This is a useful parameter which is presently measured either by undesirable invasive techniques or using the BOLD MR imaging technique which involves high field imaging to determine the effect of oxygen on paramagnetic iron but which has the disadvantage that to determine blood oxygen concentration the volume of blood in which the measurement was made needs to be known.

Other uses of the method of the invention will be readily apparent to the skilled person and include oxygen imaging (e.g. mapping) of, for example, the heart and arteries and of malignant tumours, for example in the brain, breast, lung, lymphoid tissues and superficial areas of the liver. In the case of oxygen imaging of tumours, success in treatment of malignant tumours by radiotherapy may be reflected in the level of oxygen in the tissue (typically an oxygen concentration of less than 0.01 mM will indicate that the tissue is necrotic and thus that treatment is likely to be ineffective).

It will also be apparent that the method of the invention will be useful in cardiology, surgery and intensive care where levels of oxygen and even perfusion can be non-invasively assessed in almost any tissue.

The manipulation of the detected MR signals in the method of the invention will generally be to generate an image data set (i.e. a data set from which an image may be generated) indicative of radical concentration and one or more image data sets indicative of radical electron relaxation times (generally $T_{1e}$, $T_{2e}$ or $T_{1e} \cdot T_{2e}$) and manipulation of these data sets and calibration with ex vivo calibration data to yield an image data set indicative of oxygen concentration. This oxygen concentration image data set can be transformed into an oxygen concentration image or can be subject to an upper or lower limit filter to identify regions of high or low oxygen concentration, which can again if desired be displayed as an image.

Broadly speaking, the Overhauser enhancement of the proton MR signal is dependent on the relaxation times $T_{1e}$ and $T_{2e}$ of the esr transition of the radical used in the method of the invention. These relaxation times themselves are dependent on the concentrations of the radical and dissolved oxygen in the body fluid as well as on the temperature and chemical nature of the body fluid. However while the Overhauser enhancement can easily be used to determine the oxygen concentration for an isolated small volume sample of known radical concentration ex vivo, the determination of oxygen concentration in vivo is complicated since the Overhauser enhancement is also strongly dependent on the sample structure for a large non-isolated sample, such as a living body, due inter alia to non-uniform radiation penetration into the large sample.

Thus although the method of the invention requires calibration data, obtained for a range of radical and oxygen concentrations in a fluid sample (e.g. blood) which corresponds to the body fluid in which oxygenation is to be determined and at a pre-set temperature (e.g. 37° C.), further data manipulation is required in order to extract the in vivo oxygen concentrations from the OMRI signals detected for the sample.

The calibration data are generated by determining Overhauser enhancement values for the radical in the selected body fluid, at the selected temperature and at a range of oxygen (and preferably also radical) concentrations. The intrinsic esr relaxation times for the radical can be determined, under the same conditions, using a conventional esr spectrometer equipped with a temperature controller, with oxygen concentration being determined using the method of Ravin et al J. Appl. Physiol. 18:784–790(1964), a method known to produce accurate and reproducible results.

In general, radical concentrations up to 0.2, preferably up to 1.0, especially up to 1.5 mM, and oxygen concentrations of up to 0.1, preferably up to 0.5 mM should be investigated to generate the calibration data.

For one preferred radical, referred to herein as the perdeuterated hydroxy trityl, such calibration of a blood sample at 37° C. showed maximum Overhauser enhancement (i.e. at infinite VHF power and infinite radical concentration) to be 192 and $T_1$ i.e. proton relaxivity to be 0.44 mM$^{-1}$s$^{-1}$. The dependence of $T_{1e}$ and $T_{2e}$ on radical and oxygen concentrations was found to fit the following linear functions:

$$2(\sqrt{3}\,\gamma_e T_{2e})^{-1} = 20 + 21.5\,C_{rad} + 428\,C_{O_2} \quad (1)$$

$$2(\sqrt{3}\,\gamma_e T_{1e})^{-1} = 10 + 3.6\,C_{rad} + 330\,C_{O_2} \quad (2)$$

$$(\gamma_e \sqrt{T_{1e}T_{2e}})^{-1} = 15 + 6.9\,C_{rad} + 319\,C_{O_2} \quad (3)$$

where $\gamma_e$ is the electron gyromagnetic ratio, $C_{rad}$ is the radical concentration in mM, $C_{O_2}$ is the oxygen concentration in mM and $T_{1e}$ and $T_{2e}$ are electron relaxation times in s, and coefficients are in mG, the units in which linewidth is measured.

Similar equations can be derived experimentally for whatever radical is used in the method of the invention.

With this calibration data, if $T_{1e}$, $T_{2e}$ or $T_{1e}.T_{2e}$ are calculated for a pixel in the sample's OMRI image then equations (1), (2) or (3) can easily be used to determine the oxygen concentration for that pixel. The radical concentration can be determined by manipulation of the MR signals detected in the method of the invention whereby to generate a radical concentration image data set.

However, the $T_{1e}$, $T_{2e}$ or $T_{1e}.T_{2e}$ values for the pixel must be extracted from the OMRI signals detected in the imaging procedure. The OMRI imaging sequence used in the method of the invention may be any one of the conventional sequences. However an example of one such usable sequence is shown schematically in FIG. 1. This sequence involves a VHF irradiation period ($T_{VHF}$) of approximately the same magnitude as $T_1$ for the water proton, and a single echo of time TE much less than $T_2$. Pixel intensity (I) is then given by equation (4):

$$I \alpha (1-\exp(-T_{VHF}/T_1)) \quad (4)$$

During VHF irradiation, dynamic proton polarization $<I_z>$ occurs. The steady state is governed by the Overhauser equation (5)

$$\frac{\langle I_z \rangle}{I_o} = 1 - \left[\frac{S_o k \cdot f}{I_o} \cdot \frac{S_o - \langle S_z \rangle}{S_o}\right] \quad (5)$$

where $$\frac{S_o}{I_o}$$

is equal to 658 for an electron: proton dynamic nuclear polarization ($I_o$ here represents the equilibrium magnetisation), k is the coupling factor (equal to ½ at low field), f is the leakage factor, and $(S_o-<S_z>)/S_o$ is the degree of saturation (SAT) of the electron spin transition).

The leakage factor f is given by equation (6)

$$f = \frac{rC_{rad}T_{10}}{1+rC_{rad}T_{10}} = rcT_{10} \quad (6)$$

(where r is the relaxivity of the radical;

$C_{rad}$ is the radical concentration, and $T_{10}$ is the proton relaxation time $T_1$ in the absence of the radical).

The pixel intensity of the final image is given by equation (7)

$$I \alpha (1-\exp(-T_{VHF}/T_1))(1-329 r C_{rad} T_1 SAT) I_o \quad (7)$$

(where $I_o$ is the intensity of the native image pixel)

As can be seen from a Taylorian expansion of the exponential function in equation (7), provided that $T_{VHF}$ is significantly less than $T_{10}$, $T_1$ disappears to a first order. SAT depends on the strength of the exciting VHF field $B_{1e}$ and obeys the basic Bloch equations. Where the esr transition is a single Lorentzian this means that SAT is given by equation (8)

$$SAT = \frac{\alpha P \gamma_e^2 T_{1e} T_{2e}}{1 + \alpha P \gamma_e^2 T_{1e} T_{2e} + (\Delta \omega T_{2e})^2} \quad (8)$$

(where

α is a conversion factor;

P is the VHF power; and

Δω is the distance from resonance of the off-resonance VHF excitation frequency (where an on-resonance frequency is used, Δω is of course zero)).

The conversion factor α is strongly spatially variant in in vivo large sample images, and thus knowledge of P, SAT, $\gamma_e$ and Δω is not in itself sufficient to enable oxygen concentration to be determined.

In most cases, moreover, the esr transition will not be a single Lorentzian due to residual magnetic couplings within the radical molecule. Where, as in the case with narrow esr linewidth radicals such as the trityls mentioned herein, the coupling constants are much smaller than the linewidth, the resonance lineshape will become a Voigt function and SAT will be the integral of all off-resonance values weighted by a Gaussian intensity function as in equation (9)

$$SAT = 1 - \sqrt{\frac{2}{\pi}} \frac{1}{\Delta H_{pp}^G} \int_{-\infty}^{\infty} \exp(-2H'^2/\Delta H_{pp}^{G2}) \frac{1 + \frac{4}{3}(\Delta H - H')^2/\Delta H_{pp}^{L2}}{1 + \frac{4}{3}(\Delta H - H')^2/\Delta H_{pp}^{L2} + \frac{2}{\sqrt{3}}\alpha P\gamma_e T_{1e}/\Delta H_{pp}^L} dH' \qquad (9)$$

(where $\Delta H_{PP}^G$ and $\Delta H_{PP}^L$ are the first derivative peak-to-linewidth of the Gaussian and Lorentzian functions and in field units $\Delta H$ is the off-resonance field).

Equations (8) and (9) apply to single esr peaks homogeneously or inhomogeneously broadened respectively. For well separated peaks, with large couplings, the saturation degree will be reduced by a factor corresponding to the far-off-resonance fraction (⅓ for nitroxides due to nitrogen coupling and 0.8 for trityls due to multiple $^{13}C$ couplings).

In the method of the invention, the data manipulation will in general be to fit SAT as determined on a pixel-by-pixel basis to one of equations (8) or (9) and thereby extract $T_{1e}$, $T_{2e}$ or $T_{1e} \cdot T_{2e}$, again on a pixel-by-pixel basis so permitting pixel oxygen concentration to be calculated from equations (1), (2) or (3) (or the appropriate equivalent equation for the radical used in the method).

In one preferred embodiment of the method of the invention, data manipulation is effected to calculate esr linewidth based on inhomogeneous broadening (equation (9)).

At its most elementary, this method requires three OMRI images to be generated. These however can be and preferably are supplemented with further images recorded off-resonance, and also preferably are supplemented by images recorded with different irradiation times and native images.

In the elementary version of the method images A, B and C are recorded as follows:

A: VHF power $P_A$. $\Delta\omega=0$ (i.e. on-resonance) $\Delta H=0$. Irradiation time $T_{VHF}=T_{VHF1}$ B: VHF power $P_B$ ($\neq P_A$). $\Delta\omega=0$. Irradiation time $T_{VHF}=T_{VHF1}$ C: VHF power $P_C$ (e.g.=$P_A$ or =$P_B$). $\Delta\omega\neq 0$ (i.e. off-resonance) $\Delta H\neq 0$ (e.g. 100–200 mG). Irradiation time $T_{VHF}=T_{VHF1}$ Under these conditions, pixel intensity can be written as:

$$I = A\left\{1 - \sqrt{\frac{2}{\pi}} \frac{1}{\Delta H_{pp}^G} \int_{-\infty}^{\infty} \exp(-2H'^2/\Delta H_{pp}^{G2}) \frac{1 + \frac{4}{3}(\Delta H - H')^2/\Delta H_{pp}^{L2}}{1 + \frac{4}{3}(\Delta H - H')^2/\Delta H_{pp}^{L2} + \frac{2}{\sqrt{3}}\alpha P\gamma_e T_{1e}/\Delta H_{pp}^L} \cdot dH'\right\} - B \qquad (10)$$

(where A=Gain×proton density×$rC_{rad}T_1$×(1−exp(−$T_{VHF}/T_1$)) for $rC_{rad}T_1 \ll 1$
(Gain is the system gain factor and proton density is the proton density of the pixel);
and B=Gain×proton density×(1−exp(−$T_{VHF}/T_1$))).

Equation 10 contains five unknowns: $T_1$, proton density, $C_{rad}$, $$\Delta H_{pp}^L = \frac{2}{\sqrt{3}\,\gamma_e \cdot T_{2e}}$$

and $\alpha T_{1e}$.

With a large enhancement (e.g. about 10), short $T_{VHF1}$ relative to $T_1$ and essentially uniform proton density in the fluid medium in which the radical is distributed, B can be omitted and the three unknowns $C_{rad}$, $\Delta H_{PP}^L$ and $\alpha T_{1e}$ can be fitted on a pixel-by-pixel basis from the three values of I obtained from images A, B and C respectively. Radical concentration ($C_{rad}$) can then be determined by scaling A with Gain and r to yield a radical concentration image. Using the determined value of $\Delta H_{PP}^L$ and the radical concentration image, the oxygen concentration image can then be calculated from equation (1).

A more accurate determination of oxygen concentration can be made using this method if two further images are generated, one image D on-resonance, at power $P_A$ and at irradiation time $T_{VHF}=T_{VHF2}$ (where $T_{VHF2}\neq T_{VHF1}$, e.g. $T_{VHF2}=\times 2 T_{VHF1}$), and the second image E without VHF stimulation, using conventional MR with repetition time TR=$T_{VHF1}$. Image E gives the native intensity $I_o$ for the pixels.

From the five values for pixel intensity all five unknowns can be calculated, again yielding a concentration image and $\Delta H_{PP}^L$ from which an oxygen concentration image can be determined using equation (1).

In this method, if reference samples containing body fluid and radical, are disposed about the sample surface (e.g. tubes of blood containing the radical at known concentration), the oxygen concentration image can be adjusted to express concentration even more accurately.

A further preferred embodiment of the method of the invention takes advantage of the greater sensitivity to oxygen concentration of equation (3), i.e. of the product $T_{1e} \cdot T_{2e}$. This method however requires $\alpha$, which gives the VHF magnetic field at the pixel, to be determined.

In this further method, oxygen concentration and radical concentration images are calculated from three or more images as above, a $1/T_{1e}$ image is calculated from these images and an $\alpha$-image is calculated by multiplying the $1/T_{1e}$ image by $\alpha T_{1e}$ as determined. The $\alpha$-image is then smoothed using for example a polynomial function. It is preferred that reference samples be disposed about the sample under investigation as discussed above. If this is done then the smoothing of the $\alpha$ image can be achieved using a smoothing function with fixed values at the reference sample sites. This reduces statistical error in the images, is justified as the spatial variance of $\alpha$ is slow and, with fixed reference points, produces an accurate $\alpha$ image.

Using this $\alpha$-image, the product of $\Delta H_{PP}^L$ and $1/T_{1e}$ can be calculated and from this (which is dependant on $1/T_{1e} \cdot T_{2e}$) and the radical concentration image, a more precise oxygen image can be calculated.

If reference sample tubes are not used, then the smoothed $\alpha$-image can still be calculated but in this event the $\alpha$-values determined are preferably used in the calculation of the three (or five) variables from the detected OMRI images with a further smoothed α-image being calculated from the resulting $1/T_{1e}$ image and with the procedure being repeated until successively generated α-images are essentially unchanged (i.e. the procedure converges to a best-fit).

The various methods of calculation applied to the data collected in the method according to the invention represent a significant step forward in the accurate determination of oxygen concentration in a sample. Whilst for radicals (typically nitroxides) having a large esr linewidth the Lorentzian model is an accurate approximation for the lineshape, in the case of narrow esr linewidth radicals more precise analysis of the lineshape is called for and leads to a more accurate determination of the oxygen concentration.

Thus the method according to the invention leads to an agreement factor between actual and calculated oxygen concentration typically less than or equal to about 5% for a 3×3×10 mm voxel, 100 second acquisition time, 0–0.1 mM oxygen concentration and radical dosage of 0.1–0.2 mmol/kg bodyweight, for samples being typically of the size of a human body.

In allowing the spatial variation of the VHF magnetic field to be calculated, the further method described above yields an absolute quantification of the longitudinal relation time (or the product of the longitudinal and transverse relaxation time). The longitudinal relaxation time (and even more so the product of the longitudinal and transverse relaxation rates) is more sensitive to oxygen and so this method overall is the more sensitive technique.

Although the above described methods have focused on the use of Voigt functions to calculate the various unknown parameters, the method of the invention may equally involve the use of Lorentzian functions where these are an accurate model of the esr lineshape and such a method forms a further embodiment of the invention. For example, in large linewidth radicals (typically nitroxide radicals) the effects of inhomogeneity may be neglected and the lineshape will essentially be Lorentzian. Thus in this preferred embodiment, the data manipulation step will essentially amount to fitting SAT (as determined on a pixel-by-pixel basis) to equation (8), extracting $T_{1e}$, $T_{2e}$ and $T_{1e} \cdot T_{2e}$ on a pixel-by-pixel basis thereby permitting oxygen concentration to be determined from empirical relationships such as equations (1), (2) and (3).

In practice, it may be necessary to compensate for flow effects in the method of the invention and the appropriate steps will be known to those skilled in the art. Other parameters such as for example sample viscosity, pH, temperature, radical self-broadening, etc. are typically only secondary effects and thus may be neglected when compared to the first order effects of paramagnetic oxygen in the method of the invention. Radical self-broadening is however corrected for in equations 1 to 3.

Generally speaking, for the present method any conventional persistent free radical may be used provided it is stable under physiological conditions, has a sufficiently long half life (at least one minute, preferably at least one hour), has a long electronic relaxation time and good relaxivity. It will be apparent from the discussion of the method of the invention that the sensitivity of the oxygen measurement will be improved with radicals having narrow linewidth esr transitions, e.g. up to 500 mG, preferably less than 150 mG, especially less than 60 mG. By way of illustration, for a typical oxygen sensitivity in terms of line broadening of 500 mG/mMO$_2$, a radical with a $T_{2e}$ related linewidth of 500 mG (for example nitroxide radicals of the type proposed by Lurie et al in J. Mag. Reson. 76:366–370(1988)) would give only a 10% increase in linewidth for an increase in oxygen concentration of 0.1 mM, whereas for a radical with a linewidth of 50 mG there would be a 100% increase for an equivalent increase in oxygen concentration.

Preferably, the radical selected for use in the present method should distribute substantially into the extracellular fluid (i.e. should be an ECF agent) since the effects of paramagnetic iron (e.g. the iron within the red blood cells) may be avoided there.

Another preferred characteristic of the radicals for use in the present method is that they should have a low self-broadening effect, preferably less than 100 mG, especially preferably between 0 and 50 mG per mM of the radical itself.

One particularly preferred class of compounds exhibiting low esr linewidths and self-broadening effects particularly suited to the present method is the triarylmethyl radicals (hereinafter referred to as "trityls") as discussed in WO-A-91/12024, U.S. patent application Ser. No. 08/220,522 and U.S. patent application Ser. No. 08/467,273 (Nycomed Innovation AB) and International Patent Application No. PCT/GB95/02151 of Nycomed Imaging AS as well as their deuterated analogs.

Especially preferred trityls for use in the method of the invention are those of formula:

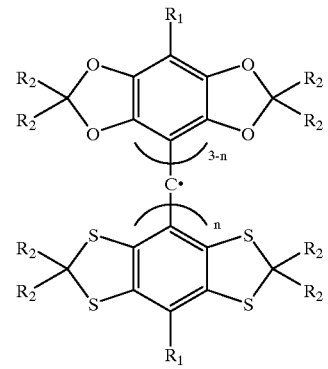

wherein:

n is 0, 1, 2 or 3;

$R^1$ is a carboxyl group or a derivative thereof;

$R^2$ is an optionally hydroxylated $C_{1-6}$-alkyl group; preferably a $C^nH_3$ or $C^nH_2OH$ group (where n is 1 or 2 i.e. $^2H$ is deuterium); and the salts and precursors and deuterated analogs thereof.

Naturally, this definition is intended to cover radical precursors which may undergo a radical generation step shortly before administration or even in situ to produce the free radical. Radical precursors and radical generation steps are well-known to those skilled in the art. Especially preferred trityls are those of the following formulae (herein referred to as perdeuterated trityl, non-deuterated hydroxy trityl, deuterated hydroxy trityl and symmetric trityl respectively):

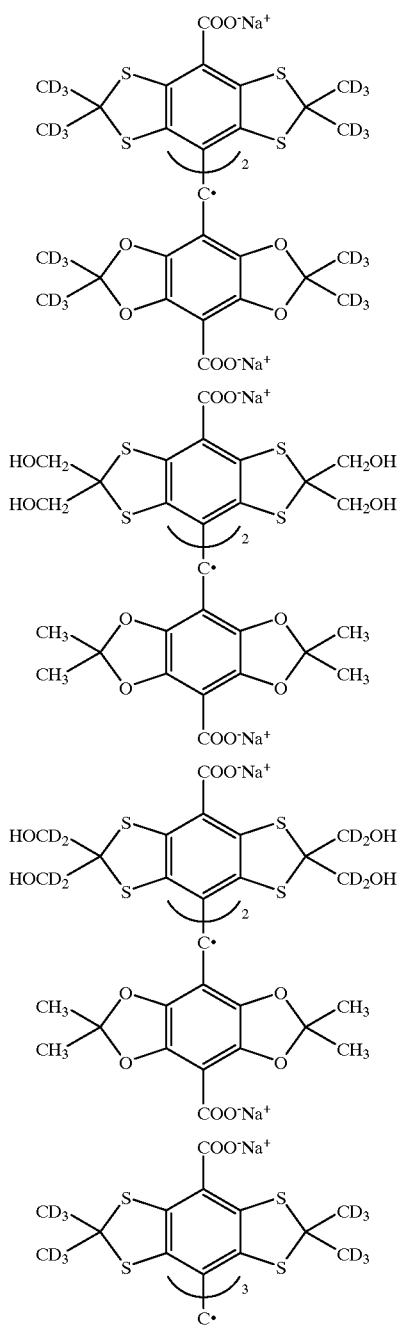

The preparation of free radicals appropriate for use in the present method is in many cases a well known synthetic procedure and in other cases is discussed for example in WO-A-91/12024, U.S. patent application Ser. No. 08/220,522 and U.S. patent application Ser. No. 08/467,273 (Nycomed Innovation AB). Perdeuterated trityl may be prepared by the method described for the preparation of its non-deuterated analogue in Examples 15 to 20 below but with the use of acetone-$d_6$ instead of acetone in the initial ketalisation step (described in Example 2 of WO-A-91/12024). Deuterated hydroxy trityl is prepared generally by successive steps of fused ring formation and deuterative reduction followed by analogous steps to those described for the preparation of the non-deuterated analogue in Examples 23 to 27 below.

The perdueterated trityl and deuterated hydroxy trityl are novel compounds and form a further aspect of the invention.

Another particularly useful class of radical compounds for the method of the invention are the deuterated nitroxide radicals, especially perdeuterated 2,5-di-t-butyl-3,4-dimethoxycarbonyl-pyrryloxyls which have remarkably low linewidths. These compounds may be prepared from 2,5-di-t-butyl-3,4-dimethoxycarbonyl-pyrryloxyl by deuterating the methyl ester moiety by transesterification with methanol-$d_4$ and/or the t-butyl groups via a multistep sequence starting from acetone-d6.

For in vivo imaging, the radical compound should of course be a physiologically tolerable radical or one presented in a physiologically tolerable form (e.g. in solution, encapsulated or as a precursor). The radicals may be conveniently formulated into contrast media together with conventional pharmaceutical carriers or excipients.

Contrast media used according to this invention may contain, besides the inert free radicals (or the non-radical precursor where radical formation is to be effected immediately before administration), formulation aids such as are conventional for therapeutic and diagnostic compositions in human or veterinary medicine. Thus the media may for example include solubilizing agents, emulsifiers, viscosity enhancers, buffers, etc. The media may be in forms suitable for parenteral (e.g. intravenous) or enteral (e.g. oral) application, for example for application directly into body cavities having external voidance ducts (such as the gastrointestinal tract the bladder and the uterus), or for injection or infusion into the cardiovascular system, muscle or other tissue. However solutions, suspension and dispersions in physiological tolerable media will generally be preferred.

For use in in vivo diagnostic imaging, the medium, which preferably will be substantially isotonic, may conveniently be administered at a concentration sufficient to yield a 1 micromolar to 10 mM preferably 0.05 to 1 mM, especially 0.1 to 0.3 mM concentration of the free radical in the imaging zone; however the precise concentration and dosage will of course depend upon a range of factors such as toxicity, the organ targeting ability of the contrast agent, and the administration route. The optimum concentration for the free radical represents a balance between various factors. In general, optimum concentrations would in most cases lie in the range 0.1 to 100 mM, especially 0.2 to 10 mM, more especially 0.5 to 5 mM. Compositions for intravenous administration would preferably contain the free radical in concentrations of 1 to 1000 mM especially 5 to 500 mM. For ionic materials, the concentration will particularly preferably be in the range 5 to 200 mM, especially 10 to 150 mM and for non-ionic materials 20 to 400 mM, especially 30 to 300 mM.

Thus viewed from a different aspect the present invention provides the use of persistent free radicals, preferably radicals of low intrinsic esr linewidth, particularly preferably trityl radicals, in in vivo oximetry.

The following Examples are intended to illustrate the invention in an non-limiting manner.

EXAMPLES

The following four water soluble, single ESR line trityls were investigated by NMRD, Dynamic Nuclear Polarisation (DNP) and ESR (Examples 1–4).

(1) Bis-(8-sodium carboxylate-2,2,6,6-tetrakis-($^2$H$_3$methyl)-benzo[1,2-d:4,5-d']-bis(1,3)-dithiole-4-yl)-mono-(8-sodium carboxylate-2,2,6,6-tetrakis-($^2$H$_3$-methyl)-benzo[1,2-d:4,5-d']-bis(1,3)-dioxole-4-yl) methyl Herein referred to as perdeuterated trityl (MW=1080).

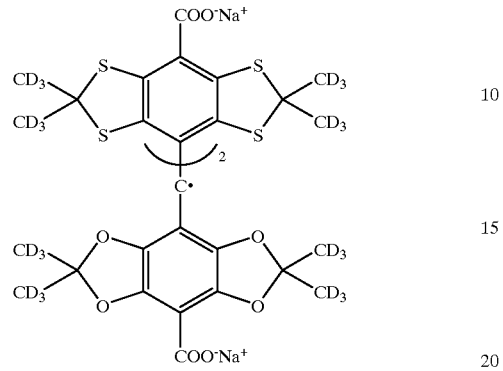

(2) Bis-(8-sodium carboxylate-2,2,6,6-tetrahydroxymethylbenzo [1,2-d:4,5-d']-bis(1,3) dithiole-4-yl)-mono-(8-sodium carboxylate-2,2,6,6-tetramethylbenzo [1,2-d:4,5-d']-bis(1,3) dioxole-4-yl) methyl Herein referred to as non-deuterated hydroxy trityl (MW= 1129).

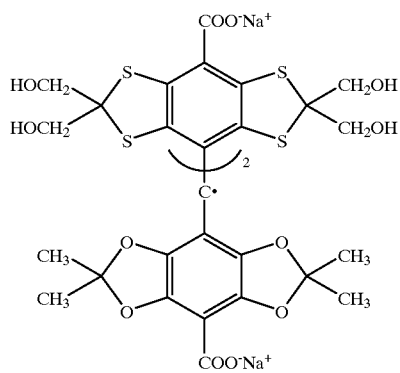

(3) Bis-(8-sodium carboxylate-2,2,6,6-tetrakis-(hydroxy-$^2$H$_2$-methyl)-benzo[1,2-d:4,5-d']-bis(1,3) dithiole-4-yl)-mono-(8-sodium carboxylate-2,2,6,6-tetramethylbenzo [1,2-d:4,5-d']-bis(1,3) dioxole-4-yl) methyl Herein referred to as deuterated hydroxy trityl (MW= 1145).

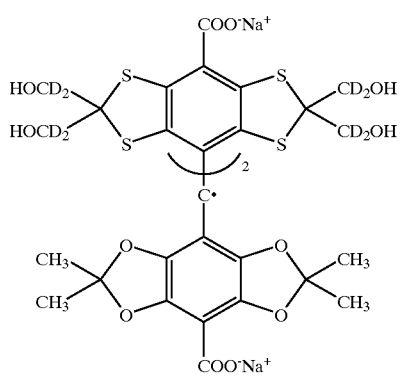

(4) Tris-(8-sodium carboxylate-2,2,6,6-tetrakis-($^2$H$_3$-methyl)-benzo[1,2-d:4,5-d']-bis(1,3) dithiole)methyl Herein referred to as symmetric trityl (MW=1151).

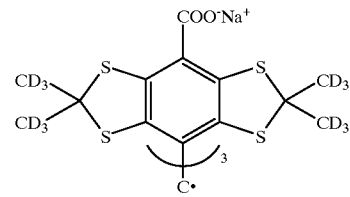

Example 1

The relaxivity and DNP enhancement data were measured in water, plasma and blood at 23° C. and 37° C. The results are set out in Tables 1 and 2.

TABLE 1

Parameters from the NMRD profiles and DNP enhancement curves of the deuterated hydroxy trityl in plasma and blood

|  | Relaxivity at 400kHz [mM$^{-1}$s$^{-1}$] | Relaxivity at infinite concentration and power [mM$^{-1}$s$^{-1}$] | A. (infinite concentration and power) |
|---|---|---|---|
| plasma |  |  |  |
| 23° C. | 0.48 |  |  |
| 37° C. | 0.45 | 0.32 | 231 |
| blood |  |  |  |
| 23° C. | 0.53 |  |  |
| 37° C. | 0.44 | 0.44 | 192 |

TABLE 2

Relaxivities and enhancements at infinite concentration and power for three radicals in water

|  | Perdeuterated trityl | Deuterated hydroxy trityl | Symmetric trityl |
|---|---|---|---|
| Relaxivity [mM$^{-1}$s$^{-1}$] |  |  |  |
| 23° C. | 0.19 | 0.26 | 0.21 |
| 37° C. | 0.14 | 0.20 | 0.15 |
| A. | 267 | 278 | 266 |

Example 2

Electron spin relaxation rates were measured by analysis of CW ESR spectra and DNP data at 23° C. and 37° C. in water, isotonic saline, plasma and blood for the deuterated hydroxy trityl and in water and isotonic saline for the perdeuterated and symmetric trityl. The results are set out in Table 3:

TABLE 3

Concentration dependent relaxation rates in isotonic saline water for three radicals in water expressed in mG/mM peak-to-peak values and in plasma and blood at 37° C. for the deuterated hydroxy trityl

|  |  | Perdeuterated trityl | Deuterated hydroxy trityl | Symmetric trityl |
|---|---|---|---|---|
| water | 23° C. | 24.3 ± 0.8 | 11.1 ± 0.5 | 35.4 ± 0.6 |
| $2(\sqrt{3}\gamma_e T_{2e})^{-1}$ | 37° C. | 28.2 ± 1.2 | 8.0 ± 0.2 | 33.1 ± 0.3 |
| water | 23° C. | 10.6 ± 0.8 | 2.6 ± 0.1 | 13.2 ± 0.5 |
| $2(\sqrt{3}\gamma_e T_{1e})^{-1}$ | 37° C. | 12.9 ± 0.3 | 2.8 ± 0.2 | 17.7 ± 0.8 |
| plasma | $2(\sqrt{3}\gamma_e T_{2e})^{-1}$ |  | 9.8 ± 0.5 |  |
| 37° C. | $2(\sqrt{3}\gamma_e T_{1e})^{-1}$ |  | 2.7 ± 0.5 |  |
| blood | $2(\sqrt{3}\gamma_e T_{2e})^{-1}$ |  | 21.5 ± 0.5 |  |
| 37° C. | $2(\sqrt{3}\gamma_e T_{1e})^{-1}$ |  | 3.6 ± 0.5 |  |

Example 3

Oximetric calibrations were made for the perdeuterated trityl and the non-deuterated hydroxy trityl in water and plasma at 37° C. with ESR in the X-band at 9 GHz. The experiment was performed on a Varian X-band spectrometer with temperature controller. A thermocouple was placed near the microwave cavity for accurate determination of the temperature. The samples were placed in thin wall teflon capillaries for rapid equilibration with a flowing gas mixture. A Sensormedics Oxygen Analyzer OM-11 was used to determine the oxygen percentage in the flowing gas. The gas pressure for temperature control and oxygenation was maintained at 20 psi. The linewidth and the saturation of the electron spin resonance was measured. Fremys salt was chosen as a $B_1$ calibration standard and a conversion factor of 38.6±0.2 mG/$\sqrt{mW}$ was obtained.

Figure 2:
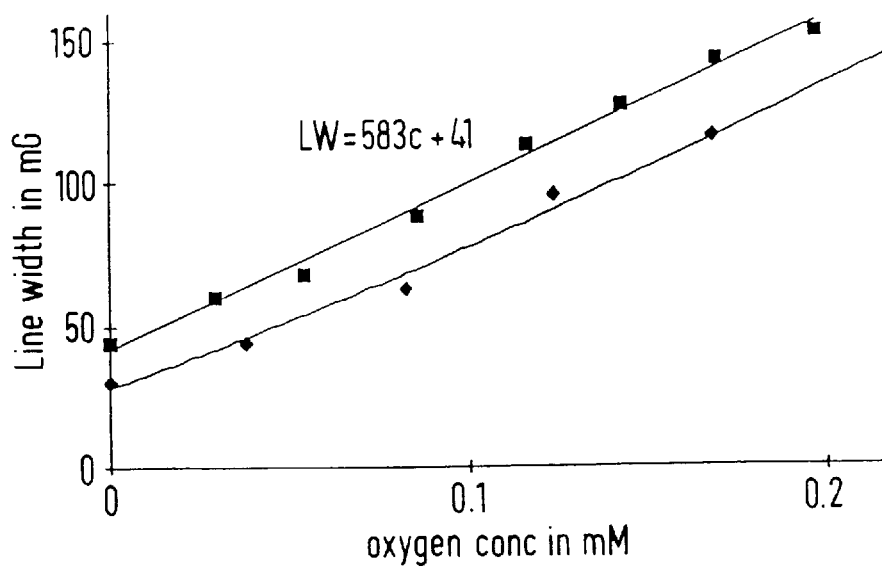
FIG. 2 shows the linewidth as a function of oxygen concentration measured at X-band for perdeuterated trityl in water and plasma.
Figure 3:
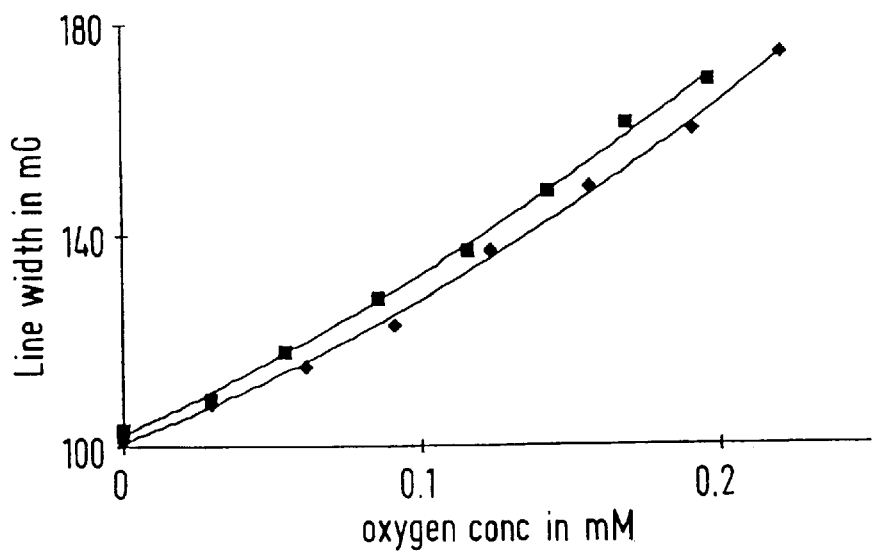
FIG. 3 shows the linewidth as a function of oxygen concentration measured at X-band for non-deuterated hydroxy trityl in water and plasma.
Figure 4:
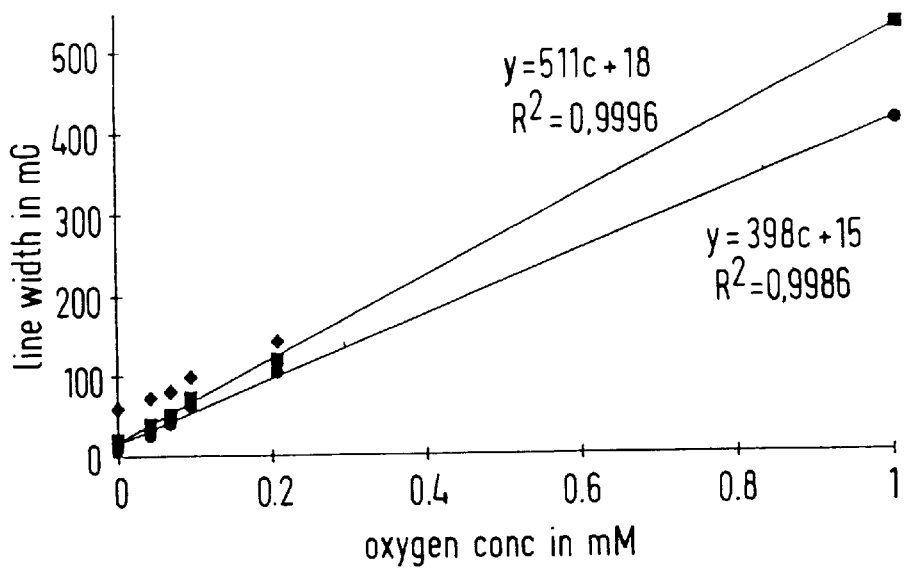
FIG. 4 shows the oxygen sensitivity of deuterated hydroxy trityl in water at 37° C.
Figure 5:
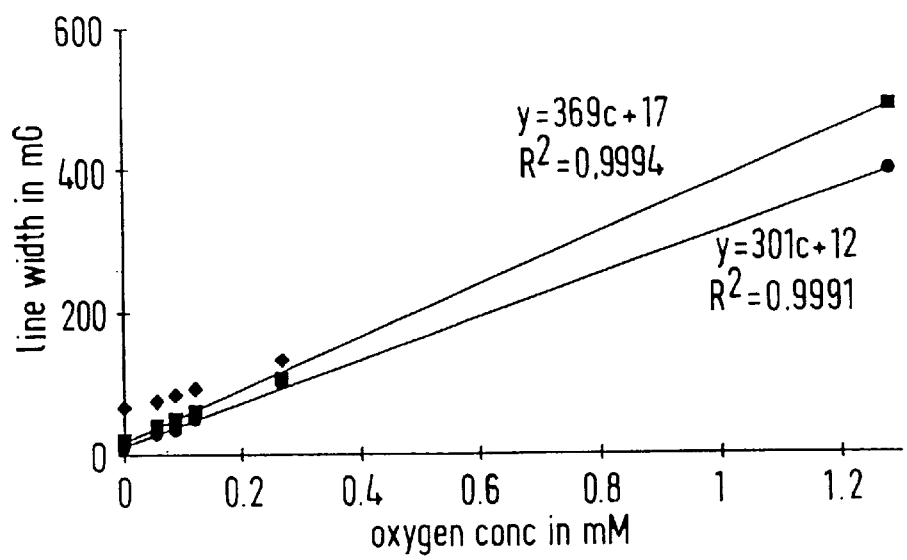
FIG. 5 shows the oxygen sensitivity of deuterated hydroxy trityl in water at 23° C.
Figure 6:
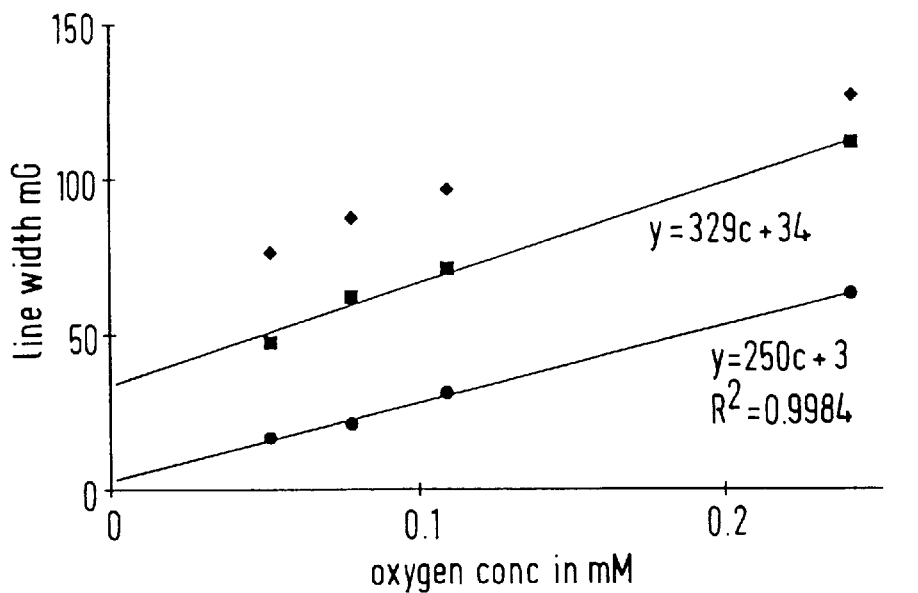
FIG. 6 shows the oxygen sensitivity of deuterated hydroxy trityl in blood at 37° C.
Figure 7:
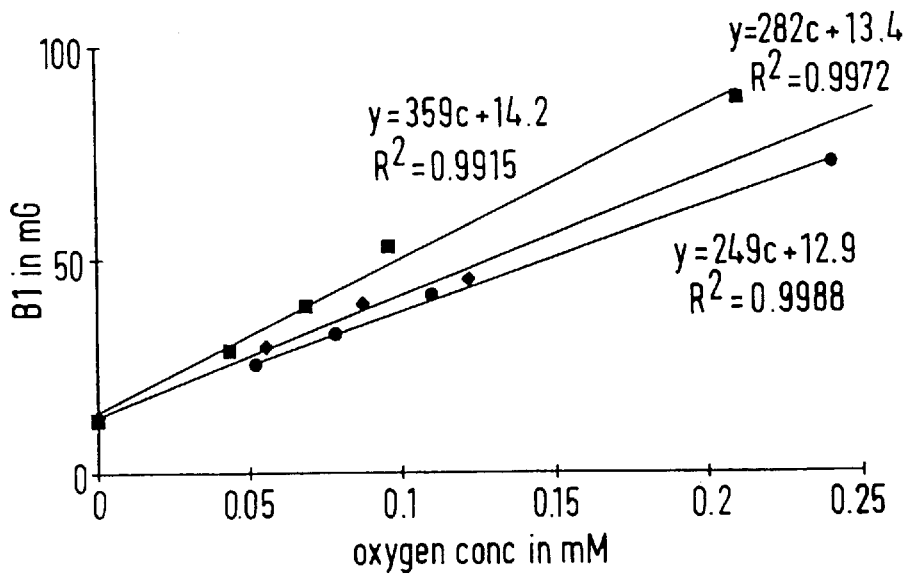
FIG. 7 shows the oxygen sensitivity of deuterated hydroxy trityl in blood at 23° C.

The results are shown in FIGS. 2 and 3 which give the linewidth as a function of oxygen concentration. The oxygen broadening of the perdeuterated trityl in plasma at 37° C. is 583 mG/mM$_{O_2}$.

Example 4

The oxygen sensitivity of the deuterated hydroxy trityl was examined at 260 MHz in water and blood at 23° C. and 37° C. by ESR and DNP. The desired oxygen partial pressures were obtained in a simple shaking tonometer. The sample of 1–2 ml volume was shaken with a water saturated gas mixture flowing slowly above the sample for 5 min. The sample and gas was in a water bath maintaining the temperature. The gas mixtures were of high purity, chemically analysed. The results are shown in FIGS. 4–7 and in Table 4. The Lorentzian line broadenings are 511 and 369 mG/mM$_{O_2}$ in water at 37° C. and 23° C. respectively and 329 mG/mM$_{O_2}$ in blood at 23° C.

TABLE 4

Relaxation rates in mG/mM peak-to-peak values and the square root of slope of the inverse DNP curve in mG/mM as a function of oxygen concentrations for the deuterated hydroxy trityl at 23° C. and 37° C. in water and blood.

|  | $(\gamma_e \sqrt{T_{1e}T_{2e}})^{-1}$ | $2(\sqrt{3}\gamma_e T_{2e})^{-1}$ | $2(\sqrt{3}\gamma_e T_{1e})^{-1}$ |
|---|---|---|---|
| water, 37° C. | $359C_{O_2} + 14.2$ | 511 | 398 |
| water, 23° C. | $282C_{O_2} + 13.4$ | 369 | 301 |
| blood, 37° C. | $319C_{O_2} + 15.0$ | 428 | 330 |
| blood, 23° C. | $249C_{O_2} + 12.9$ | 329 | 250 |

Example 5

The following experiments were performed using the hydroxy trityl radical (as hereinbefore defined) and carried out on a Picker Nordstar MEGA 4 250–300 MR machine adapted for use in OMRI by reduction of the primary field strength from 0.1 to 0.01T and by the incorporation of a VHF emitter to emit VHF radiation in the frequency range 200 to 300 MHz and the power range 0 to 100 W.

(a) Blood Samples with Different Radical Concentrations and Oxygen Tension

Figure 8:
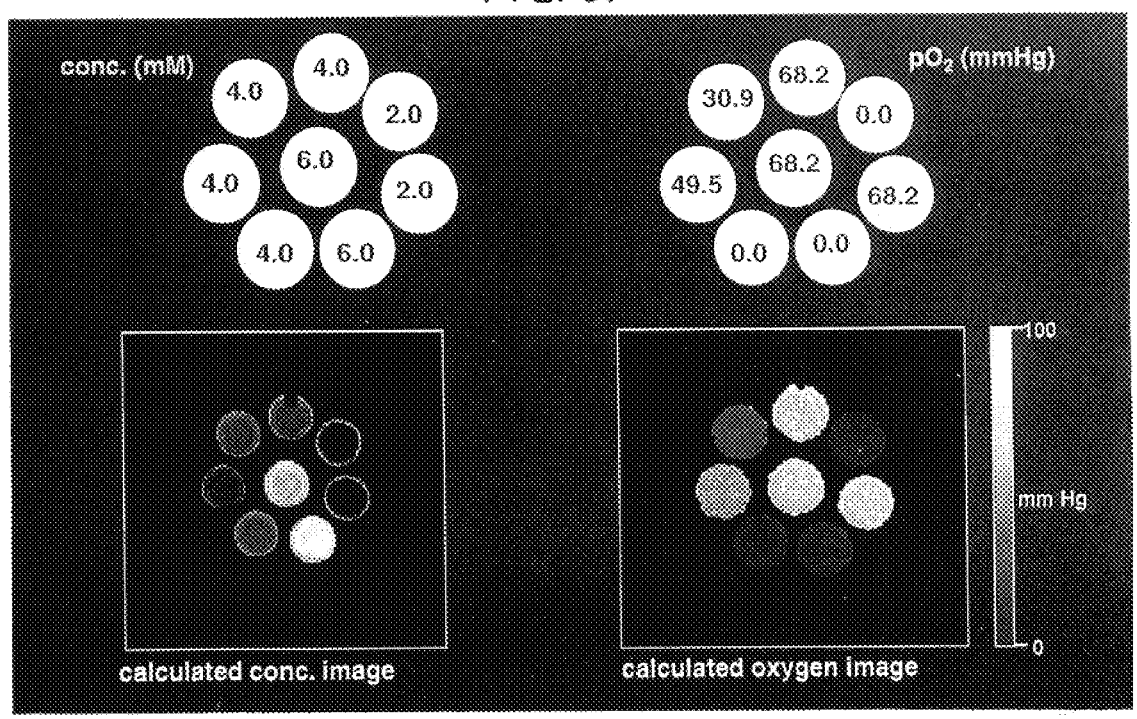
FIG. 8 shows the radical concentration and oxygen images calculated in blood samples at three different radical doses.

Radical concentration and oxygen images were calculated in blood samples at three different radical doses, 2.0 mM, 4.0 mM and 6.0 mM. The results are shown in FIG. 8.
Parameters:

| Scan time | 4:36 min |
|---|---|
| TR/TE | 270 ms/20 ms |
| Slice | 4 mm |
| Pixel size | 0.5 × 0.5 mm$^2$ |
| Average | 2 |
| T-vhf | 200 ms |
| Sampling time | 24 ms |
| Samp. freq. | 21 kHz |
| Samp. matrix | 512 × 256 |
|  | (Oversampling in read direction) |
| Recon. matrix | 256 × 256 |

(b) OMRI Oximetry

Figure 9:
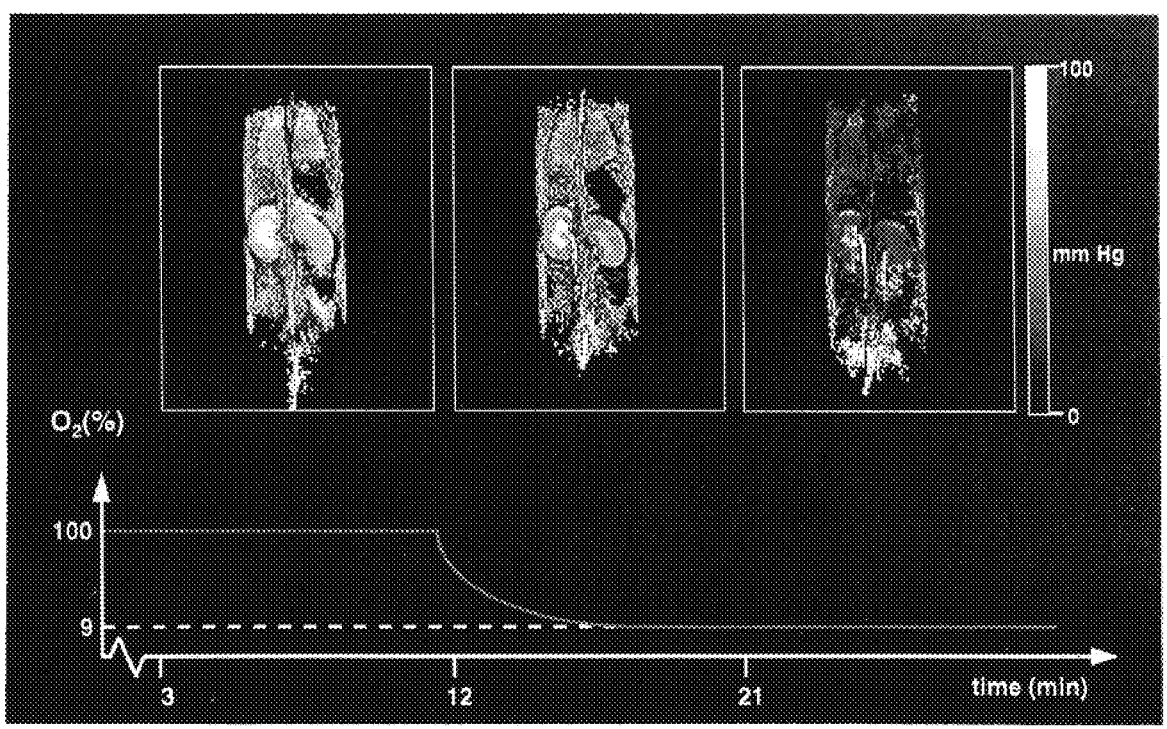
FIG. 9 shows three rat images showing in vivo oxygen concentration after inhalation of gas of varying oxygen content.

Three images of rats weighing 120 g were obtained showing in vivo oxygen concentration after inhalation of gas of varying oxygen content. The radical dose was 1.5 mmol/kg injected into the tail vein in a volume of 1.5 ml and an injection time of 10 s (10 s before the first image was obtained). The results are showing in FIG. 9.
Parameters:

| Scan time | 3:28 min |
|---|---|
| TR/TE | 270 ms/20 ms |
| Slice | 5 mm |
| Pixel size | 0.75 × 0.75 mm$^2$ |
| Average | 2 |
| T-vhf | 200 ms |
| Sampling time | 24 ms |
| Samp. freq. | 21 kHz |
| Samp. matrix | 512 × 192 |
|  | (Oversampling in read direction) |
| Recon. matrix | 192 × 192 |

(c) OMRI Oximetry

Figure 10:
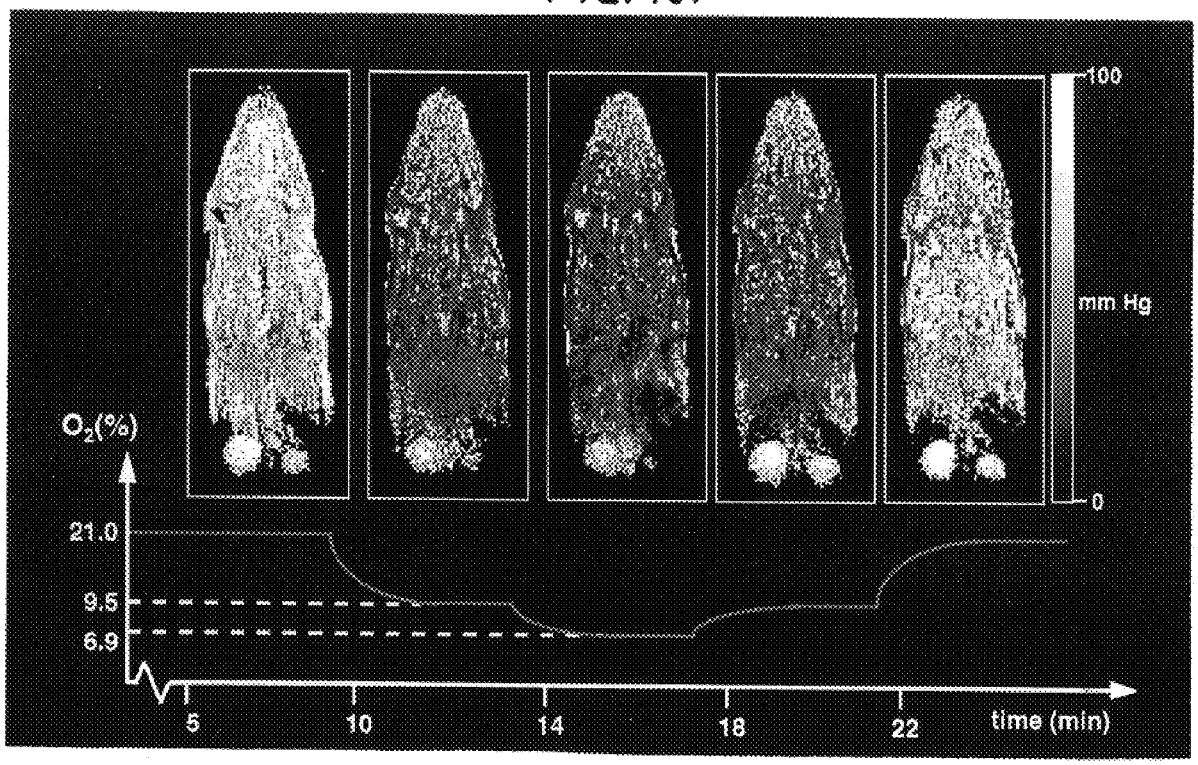
FIG. 10 shows five rat images showing in vivo oxygen concentration after inhalation of gas of varying oxygen content.

Five images of rats weighing 125 g were obtained showing in vivo oxygen concentration after inhalation of gas of varying oxygen content. The radical dose was 1.5 mmol/kg injected into the tail vein in a volume of 1.5 ml and an injection time of 15 s (15 s before the first image was obtained). The results are shown in FIG. 10.
Parameters:

| Scan time | 3:28 min |
|---|---|
| TR/TE | 270 ms/20 ms |
| Slice | 5 mm |
| Pixel size | 0.75 × 0.75 mm$^2$ |
| Average | 2 |
| T-vhf | 200 ms |
| Sampling time | 24 ms |
| Samp. freq. | 21 kHz |
| Samp. matrix | 512 × 192 (oversampling in read direction) |
| Recon. matix | 192 × 192 |

(d) OMRI Oximetry

Figure 11:
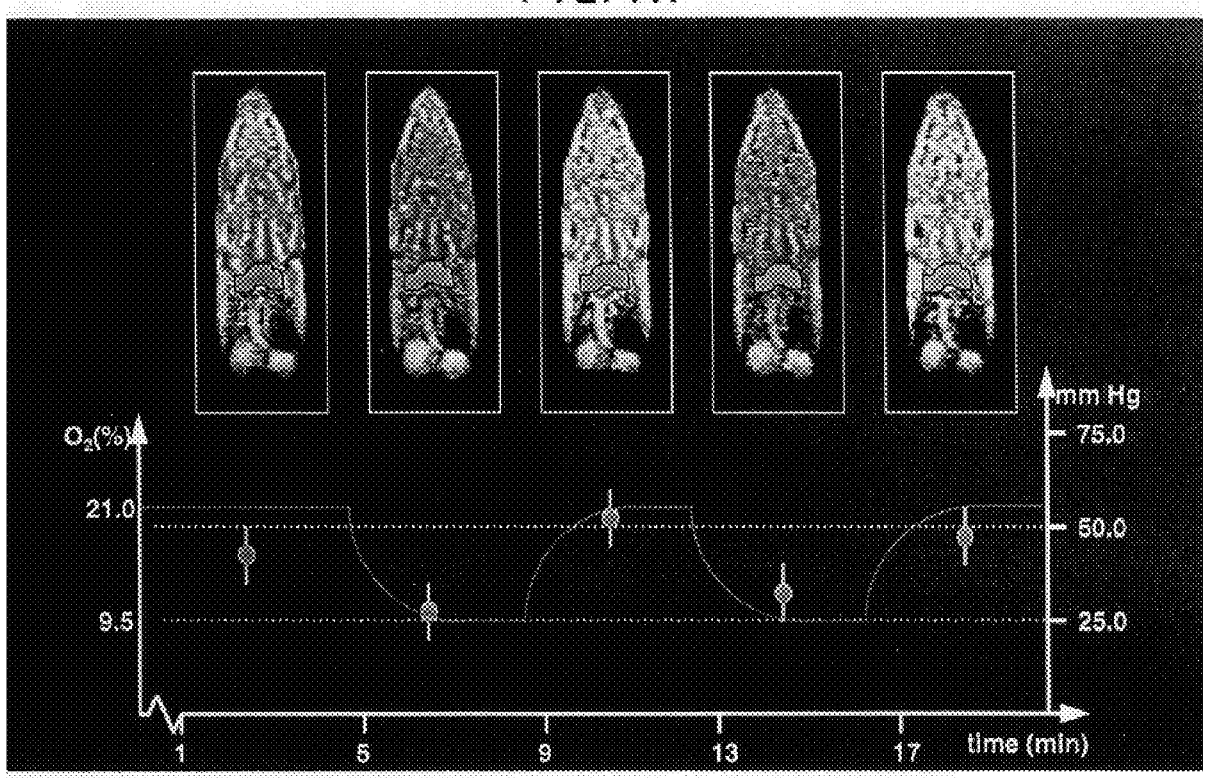
FIG. 11 shows five rat images showing the correlation between measured oxygen tension and the oxygen content in an inhaled gas.

An experiment was performed to investigate the correlation between measured oxygen tension in the lungs and the oxygen content in an inhaled gas. Rats weighing 150 g were injected in the tail vein with the radical in a dose of 1.0 mmol/kg in an injection volume of 0.5 ml and an injection time of 10 s (10 s before the first image was obtained). The results are shown in FIG. 11.

Parameters:

| | |
|---|---|
| Scan time | 1:44 min |
| TR/TE | 270 ms/18 ms |
| Slice | 5 mm |
| Pixel size | 1.0 × 2.0 mm$^2$ |
| Average | 2 |
| T-vhf | 200 ms |
| Sampling time | 24 ms |
| Samp. freq. | 21 kHz |
| Samp. matrix | 512 × 96 (Oversampling in read direction) |
| Recon. matrix | 192 × 96 |

(e) OMRI Oximetry

Figure 12:
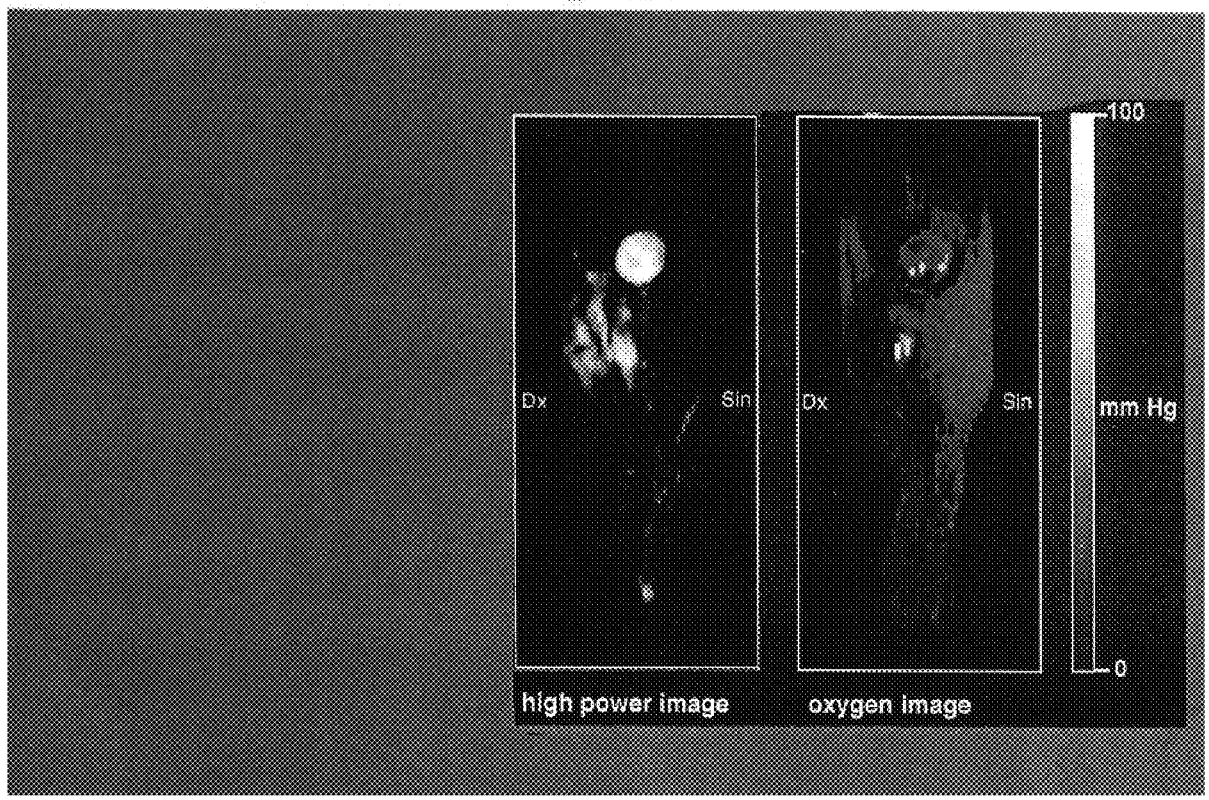
FIG. 12 shows one high power image and one calculated oxygen image of a rat after clamping.

One high power image and one calculated oxygen image were obtained after clamping. Rats weighing 132 g were injected in the tail vein with the radical in a dose of 2 mmol/kg in an injection volume of 1.0 ml and an injection time of 60 s (15 minutes before the first image was obtained). Imaging was started 8 minutes after clamping (see FIG. 12).

Parameters:

| | |
|---|---|
| Scan time | 3:28 min |
| TR/TE | 270 ms/20 ms |
| Slice | 8 mm |
| Pixel size | 1.0 × 2.0 mm$^2$ |
| Average | 2 |
| T-vhf | 200 ms |
| Sampling time | 24 ms |
| Samp. freq. | 21 kHz |
| Samp. matrix | 512 × 192 (Oversampling in read direction) |
| Recon. matrix | 192 × 192 |

Example 6

The ESR-spectral properties of a series of partially and fully deuterated nitroxides (compounds 3b–d) also useful in the method of the invention have been investigated. These radicals are derived from 2,5-di-t-butyl-3,4-dimethoxycarbonyl-pyrryloxyl (Compound 3a) and were investigated alongside Tempone (4-oxo-2,2,6,6-tetramethyl-piperidine-1-oxyl, 1) and CTPO (3-carbamoyl-2,2,5,5-tetramethyl-pyrroline-1-yloxyl, 2a) which are typical examples of nitroxides frequently used for imaging purposes.

Materials. 4-oxo-2,2,6,6-tetramethyl-piperidine-1-oxyl, 1 (Jansen, 95%), 4-oxo-2,2,6,6-tetramethyl-piperidine-d$_{16}$-1-oxyl, 1-d$_{16}$ (MSD isotopes, 98 atom-% D) and 2,2,5,5-tetramethyl-3-pyrrolin-d$_{13}$-oxyl-3-carboxylic acid, 2b–d$_{13}$ (MSD isotopes, 97.5 atom-% D) were used as received. 2,2,5,5-tetramethyl-3-pyrrolin-1-oxyl-3-carboxylic acid, 2b, was available from earlier work. Methyl-4,4-dimethyl-3-oxo-pentanoate (Aldrich, 99%) (5a), trimethylsilyl iodide (TMSI, Jansen, 97%), acetone-d$_6$ (Glaser AG, >99.5% D) and methanol-d$_4$ (CIL, >99.8% D) were used as supplied. Pinacolone-d$_{12}$ ws prepared from acetone-d$_6$ as described in Organic Synthesis Coll., 1, 459–462 for the non-deuteraded compounds. Diethyl ether (Anhydroscan <0.01% H$_2$O) was passed through neutral alumina prior to use. Sodium hydride (Aldrich, 80% suspension in mineral oil) and nickel peroxide (Aldrich) were used as received. All other chemicals were of highest commercial quality available and used as supplied.

Instrumentation. The ESR-spectra were recorded by the Upgrade Version ESP 3220-200SH of a Bruker ER-200D SRC instrument at 22°. The radical concentration was in the range 0.1–0.2 mM and the modulation amplitude was 10 mG. The microwave power was well below saturation. NMR-spectra were recorded on a Varian XL-300 spectrometer. Mass spectra were recorded on a VG Quattor II instrument equipped with ESPC electrospray. GLC analyses were performed on a HP 5830 ser II instrument, equipped with a fused-silica column (30 m, 0.25 $\mu$m, HP-1701). TLC analyses and column chromotographic separations were performed on Silica Gel 60, using heptane/ether as the eluent.

Preparation of 5c. NaH (22.9 g, 0.77 mol) and dimethyl carbonate (64.1 g, 0.77 mol) were treated with pinacolone-d$_{12}$ (32.4 g, 0.29 mol) as described for the non-deuterated compound in J. Am. Chem. Soc., 72, 1356 (1950) to give 5c (28.1 g, 0.17 mol, 59%) boiling at 98–100° C./6 mm. $^1$H NMR (CD$_3$OD): δ 3.72 (s, 3H). $^{13}$C NMR (CD$_3$OD): δ 209.0 (—CO—), 168.8 —COO—), 51.2 (—CH$_3$), 43.7–42.0 (m, —CD$_2$), 25.0–23.5 (m, —CD$_3$).

Preparation of 5b and 5d. The methyl-h$_3$ ester (5a, 5c) was dissolved in CD$_3$OD and treated with 2 mol-% NaOCD$_3$. After evaporation the procedure was repeated, and when no protons from the methyl group were discernible by NMR the transesterification was judged to be complete. The mixture was evaporated, ether added, evaporated and used without further purification in the next step.

Preparation of 6d. To a stirred suspension of Na (1.22 g, 53 mmol) in 15 ml of ether under Ar was added 5d (8.5 g, 49 mmol) in 30 ml of ether over 2 h. After another 4 h of stirring a solution of I$_2$ (6.35 g, 25 mmol) in 50 ml of ether was added dropwise over 1 h. The mixture was left overnight and the resulting white suspension was poured onto ether/saturated aq. NaCl. The aq. layer was extracted twice with ether and the combined organic layers were dried over MgSO$_4$, evaporated and chromatographed. 4.8 g (14 mmol, 56%) 6d was collected as a colourless oil, consisting of a mixture of diastereomers and with incomplete deuteration at the two asymmetric (and acidic) carbons. $^{13}$C NMR (CD$_3$OD):209.0+208.1(—CO—), 168.5+168.2(—COO—), 53.7–53.0 (m, —CD$_2$—+—CHD—+—CH$_2$—), 51.7–50.7 (m, ester-CD$_3$), 25.0–23.5 (m, —CD$_3$). MS(ESP$^+$), m/z:379 (M+39), 363 (M+23). 6a–6c were similarly prepared from 5a–5c in 40–60% yield.

Preparation of 7d. NaOCOCH$_3$ (1.78 g, 13.0 mmol), NH$_2$OHxHCl (0.80 g, 11.5 mmol) in 13 ml H$_2$O and 6d (2.80 g, 8.2 mmol.) in 35 ml CH$_3$COOH were mixed and stirred at 65° C. for 72 h. The mixture was cooled and most of the solvent was evaporated. The residue was poured onto ether/aq. NaHCO$_3$ and the aq. layer was extracted with ether. The combined ethereal layers were dried over Na$_2$SO$_4$, and the resulting oil was chromatographed to give 1.6 g of recovered starting material, followed by the oxime (0.025 g, 0.07 mmol, 2.0%) and 7d (0.065 g, 0.19 mmol, 5.4%) as white crystals, mp. 156–158° C. $^1$H NMR NMR (CD$_3$CN): δ 9.82 (s,1H). $^{13}$C NMR(CD$_3$CN): 168.3, 136.5, 109.3, 52.2–50.9 (m, ester-CD$_3$), 33.5, 30.2–28.1 (m, t-CD$_3$). MS (ESP$^-$), m/z: 334 (M–1). Similarly prepared were: 7a $^1$H NMR ((CD$_3$)$_2$CO): δ 9.80 (S, 1H), 3.67 (s, 6H), 1.40 (s, 18H). MS (ESP$^-$), m/z: 310 (M−1). 7b. $^1$H NMR ((CD$_3$)$_2$CO): δ 9.80 (s, 1H), 1.40 (s, 18H). $^{13}$C NMR ((CD$_3$)$_2$CO): δ 167.1, 135.3, 108.7, 45.8–44.7 (m, CD$_3$), 33.4, 29.3. MS (ESP$^-$), m/z: 316 (M−1). 7c. $^1$H NMR ((CD$_3$)$_2$CO): δ 9.87 (s, 1H), 3.63 (s, 6H). 13C NMR ((CD$_3$)$_2$CO): δ 167.0, 135.5, 108.7, 50.9, 32.3, 29.7–28.2 (m, CD$_3$). MS (ESP$^-$), m/z: 328 (M−1).

Preparation of 3a–3d. 3a was prepared from the methyl ester 5a as previously described for the ethyl ester in Bull. Soc. Chim. France, 72, 4330 (1970) and 3b was prepared similarly via transesterification of 5a. The extreme unwillingness of the methyl ester moiety of 3a, 6a and 7a to transesterificate and to undergo conventional hydrolysis meant the transesterification step was performed before the dimerization step in the preparation of 3b. The preparation of 3c and 3d started with pinacolization of hexadeuteroacetone followed by pinacol rearrangement and carboxylation to give 5c, transesterification, dimerization and ring closure with hydroxylamine as summarised in Scheme 1 below. The intermediate oximes could be isolated from the reaction mixture (in yields similar to those of the ring-closed products), and these were converted into the hydroxylamines separately under otherwise identical conditions, or simply pooled in the next repetition of the synthesis. The hydrolysis of 7a was performed with TMSI in CdCl$_3$, giving the dicarboxylic acid 4 in moderate yield.

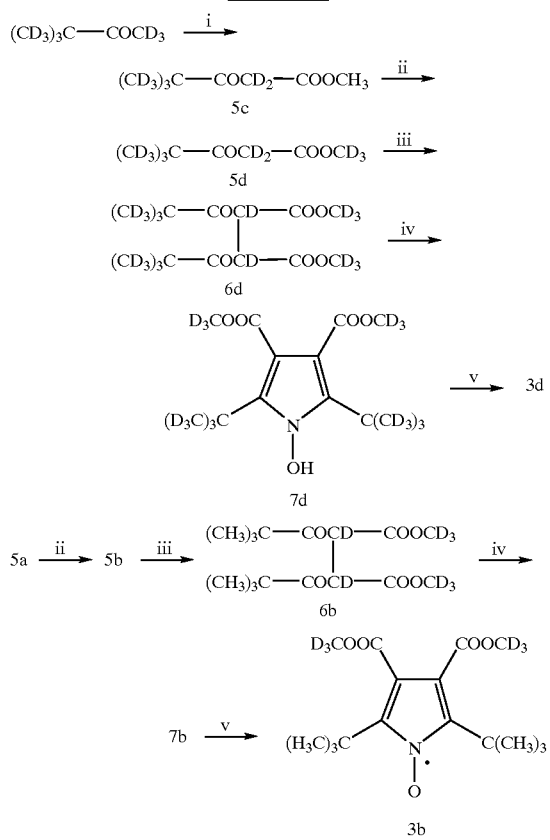

SCHEME 1

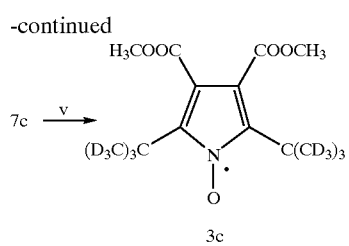

i. NaH, (CH$_3$)$_2$OCO  ii. CD$_3$OD, cat. NaOCD$_3$
iii. a) Na/ether b) I$_2$  iv. NH$_2$OH, CH$_3$COOH
v. NiOOH Preparation of pyrryloxyl radicals. To a degassed solution of 2 mg of the hydroxylamine 7a–7d in 2 ml of benzene was added ca. 10 mg NiOOH. After 5 min the suspension was filtered and the pale green blue solution was diluted with degassed benzene in order to obtain a solution suitable for ESR.

Preparation of 2.5-di-t-butyl-N-hydroxy-pyrrol-3,4-dicarboxylic acid (4)

When 7a was subjected to the transesterification conditions described above, treated with pig liver esterase or subjected to standard alkaline hydrolysis conditions no reaction was observed. 7a (0.090 g, 0.29 mmol) was dissolved in 10 ml of dry CDCl$_3$ and TMSI (0.240 g, 1.20 mmol) was added. After heating to 55° C. overnight the mixture was diluted with 40 ml of CH$_2$Cl$_2$ and washed with sat. aq. NaCl, a few drops of aq. Na$_2$S$_2$O$_4$ in sat. aq. NaCl and finally sat. aq. NaCl. After being dried over Na$_2$SO$_4$ and evaporated the remaining solid was dissolved in heptane:ether 9:1, evaporated and titurated with heptane to give the dicarboxylic acid 4 (0.040 g, 0.14 mmol, 49%) as colourless crystals. $^1$H NMR ((CD$_3$)$_2$CO):δ 1.50 (s). $^{13}$C NMR ((CD$_3$)$_2$CO):δ 159.5, 141.0, 108.2, 33.7, 29.2. MS(ESP$^-$), m/z: 264 (M−19). Upon treatment with NiOOH as described above an ESR-signal with a line width almost identical to that of 3b was recorded.

ESR-measurements. Summarised in Table 5 are the ESR line widths for the nitroxides discussed above. All spectra were recorded at high dilution in carefully degassed benzene at 22° C. Perdeuteration results in a reduction of the line width by a factor of 2.2 for 1 and of 2.5 for 2b. For nitroxides 3a–d deuteration of the alkyl groups of the ester moiety causes a decrease by a factor of 1.9 (3c:3d) whereas deuteratin of the t-butyl groups alone has almost no influence (3a:3c). The fully deuterated nitroxide 3d was found to have the most narrow line width hitherto recorded for a nitroxide, 113 mG, and a nitrogen coupling constant of 4.4 G (in benzene). The spin density distributions, nitrogen coupling constants and intrinsic line widths for 3d are compared in Table 6 to other nitroxides.

TABLE 5

ESR Line Widths of Nondeuterated and Predeuterated Nitroxides in Benzene at 23° C.

| Compound No. | Line width/mG |
|---|---|
| 1 | 602 |
| 1-d$_{16}$ | 266 |
| 2b | 1032 |
| 2b-d$_{13}$ | 407 |
| 3a | 228 |

TABLE 5-continued

ESR Line Widths of Nondeuterated and Predeuterated Nitroxides in Benzene at 23° C.

| Compound No. | Line width/mG |
|---|---|
| 3b | 172 |
| 3c | 219 |
| 3d | 113 |

TABLE 6

Spin Density Distribution, Nitrogen Coupling Constants and Intrinsic Line Widths for some Nitroxides

| | 1 | Frémys salt | $(C_6H_5)_2NO$ | 3d |
|---|---|---|---|---|
| $a_N$ | 15 | 12 | 9.7 | 4.4 |
| $pN + pO$ | 1.0 | $1.0^a$ | 0.78 | 0.60 |
| $\Delta H_1$ (mG) | 300 | 210 | 160 | ≦113 |
| $(\Delta H_1)^{1/2}$ | 17 | 14.5 | 12.6 | ≦10 |

$^a$for $_pO + _pN \leq 1$

Example 7

2,2,6,6-Tetra(ethoxycarbonyl)benzo[2-d:4,5-d']bis(1,3)dithiole

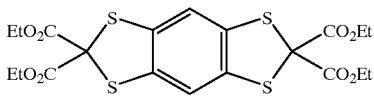

The reaction was performed under argon atmosphere using deoxygenated solvents. 1,2,4,5-Benzotetrathiole (1.50 g, 7.3 mmol) and $K_2CO_3$ (4 g) were mixed with dry DMF (70 ml) and a solution of dibromodiethyl malonate (4.26 g, 14.6 mmol) in DMF (15 ml) was added. The mixture was heated to 60° C. and stirred for 65 h. After cooling to room temperature, the reaction mixture was poured into ice water and then extracted with $CH_2Cl_2$ (2×100 ml). The combined organic phases were washed with water (4×50 ml), dried ($Na_2SO_4$) and evaporated. Yield: 3.32 g (88%) $^1H$ MMR ($CDCl_3$): 6.97 (s, 2H), 4.29 (q, J=7.2 Hz, 8H), 1.28 (t, J=7.2 Hz, 12H).

Example 8

2,2,6,6-Tetra(methoxycarbonyl)-4,8-dibromobenzo[1,2-d:4,5-d']bis(1,3)dithiole

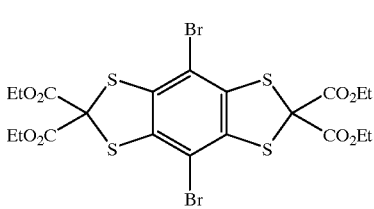

2,2,6,6-Tetra(ethoxycarbonyl)benzo[1,2-d:4,5-d']bis(1,3)-dithiole (10.7 g, 20.6 mmol) was dissolved in glacial acetic acid and bromine (16.5 g, 0.103 mol) was added. The solution was stirred at 65° C. for 17 h and aqueous $Na_2S_2O_3$ was added. The aqueous slurry was extracted with $CH_2Cl_2$ (3×100 ml), the combined organic phases were washed with water (3×50 ml), dried ($MgSO_4$) and evaporated. The residue was triturated with $CH_3CN$ and dried. Yield: 10.1 g (72%).

$^1H$ NMR (DMSO-$d_6$): 4.28 (q, J=7.2 Hz, 8H), 1.21 (t, J=7.2 Hz, 12H).

Example 9

4,8-Dibromobenzo[1,2-d:4,5-d']bis(1,3)dithiole-2,6-dispiro-(4,4-dimethyl-3,5-dioxane)

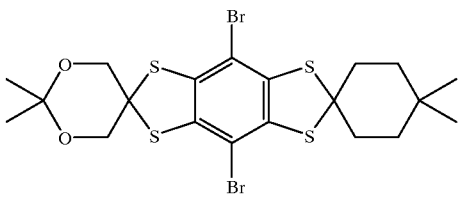

2,2,6,6-Tetra(methoxycarbonyl)-4,8-dibromobenzo[1,2-d:4,5-d']bis(1,3)dithiole (6.76 g, 10.0 mmol) was dissolved in dry THF, the solution was cooled to 0° C. and a solution of DIBAL in toluene (17.8 ml, 100 mmol) was added dropwise. The solution was heated to reflux temperature for 3 h and then allowed to cool to room temperature. Methanol (20 ml) was added dropwise followed by water (60 ml) and the pH was adjusted to 2 using aqueous 6 M HCl. The solvents, except water, were removed by evaporation and the precipitate was collected by filtration. The product was washed with water, acetonitrile, dried and then suspended in dry acetone (600 ml). $BF_3 \cdot Et_2O$ (2.52 ml, 20 mmol) was added and the solution was stirred for 20 min. Solid $K_2CO_3$ (6.0 g) was added and stirring was continued for another 5 min. After filtering through a short pad of basic alumina, the solvents were removed by evaporation, the residue was triturated with $CH_2Cl_2$ and dried. Yield: 1.12 g (19%)

$^1H$ NMR (DMSO-$D_6$): 4.15 (S, 8H), 1.37 (S, 12H).

Example 10

4-Bromobenzo[1,2-d:4,5-d']bis(1,3)dithiole-2,6-dispiro-(4,4-dimethyl-3,5-dioxane)

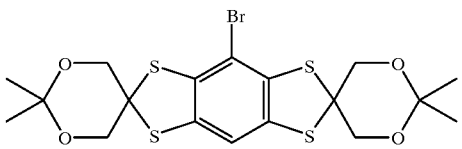

4,8-Dibromobenzo[1,2-d:4,5-d']bis(1,3)dithiole-2,6-dispiro-(4,4-dimethyl-3,5-dioxane) (1.14 g, 1.94 mmol) was dissolved in dry THF (270 ml) under an atmosphere of argon. After cooling the solution to −45° C., a solution of n-BuLi in hexane (2.5M, 2.02 mmol) was added dropwise. After stirring for 5 min, methanol (3 ml) was added, the solution was allowed to attain room temperature and the solvents were evaporated. The product was purified by chromatography on silica gel using a mixture of $CH_2Cl_2$ and methanol (99.5:0.5) as the eluent. Yield: 0.70 g (71%).

$^1H$ NMR ($CDCl_3$): 6.80 (s, 1H), 4.15 (s, 8H), 1.47 (s, 12H).

Example 11

Tris(benzo[1,2-d:4,5-d']bis(1,3)dithiole-4-yl-2,6-dispiro-(4,4-dimethyl-3,5-dioxane))methanol

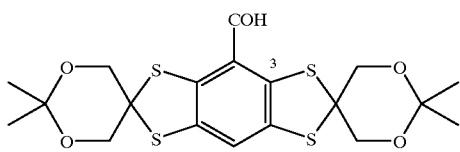

4-Bromobenzo[1,2-d:4,5-d']bis(1,3)dithiole-2,6-dispiro-(4,4-dimethyl-3,5-dioxane) (0.99 g, 1.94 mmol) was suspended in dry diethyl ether (28 ml) under an atmosphere of argon. A solution of n-BuLi (2.5M in hexane, 1.94 mmol) was added dropwise and, after 5 min, a solution of diethyl carbonate 0.078 ml, 0.64 mmol) in diethyl ether (3 ml) was added slowly. After stirring for 18 h, ethanol (5 ml) was added and the solvent was removed by evaporation. The product was purified by chromatography on silica gel using a mixture of $CHCl_3$ and ethyl acetate (20:1) as the eluent. Yield: 0.65 g (76%)

$^1$H NMR ($CDCl_3$): 7.16 (s, 3H), 6.01 (s, 1H), 3.86–4.22 (m, 24H), 1.43, 1.41, 1.37, 1.32 (4s, 36H).

Example 12

Tris(8-ethoxycarbonylbenzo[1,2-d:4,5-d']bis(1,3)dithiole-4-yl-2,6-dispiro-(4,4dimethyl-3,5-dioxane))methanol

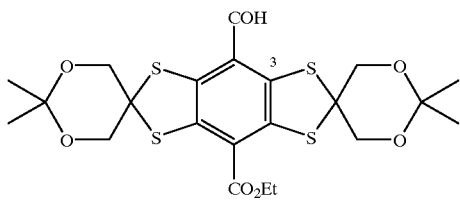

Tris(benzo[1,2-d:4,5-d']bis(1,3)dithiole-4-yl-2,6-dispiro-(4,4-dimethyl-3,5-dioxane))methanol (0.205 g, 0.156 mmol) was dissolved in dry benzene (12 ml) containing N,N N',N'-tetramethylethylene diamine (0.33 ml, 2.18 mmol) under an atmosphere of argon. A solution of t-BuLi in pentane (1.5M, 2.18 mmol) was added dropwise and stirring was continued for 40 min. The solution was then transferred into another flask, kept at 0° C. and containing diethylpyrocarbonate (1.3 ml, 8.82 mmol) and benzene (6 ml). After stirring for 45 min, an aqueous $NaH_2PO_4$ buffer was added, the organic phase was separated, washed with water and evaporated. The product was purified by preparative HPLC. Yield: 55 mg (23%).

$^1$H NMR ($CDCl_3$): 6.68 (s, 1H), 4.41–4.52 (m, 6H), 3.86–4.21 (m, 24 H), 1.22–1.60 (m, 45H).

Example 13

Tris(8-ethoxycarbonyl-2,2,6,6-tetrahydroxymethylbenzo[1,2-d:4,5-d']bis(1,3)dithiole-4-yl)methanol

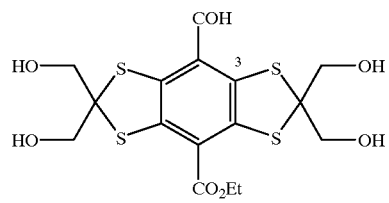

Tris(8-ethoxycarbonylbenzo[1,2-d:4,5-d']bis(1,3)dithiole-4-yl-2,6-dispiro-(4,4-dimethyl-3,5-dioxane))methanol (55 mg, 0.0359 mmol) was dissolved in a mixture of glacial acetic acid (20 ml) and water (5 ml) and the solution was stirred at room temperature for 42 h. The solvents were removed by evaporation, traces of acid were removed by addition of benzene followed by evaporation. HPLC analysis indicated >98 purity of the product. Yield: 42.4 mg (91%).

MS (ESP$^-$, m/e): 1293 (M$^+$, 68%), 1291 ([M–2]$^-$, 100%).

Example 14

Tris(8-carboxy-2,2,6,6-tetrahydroxymethylbenzo[1,2-d:4,5-d']bis(1,3)dithiole-4-yl)methyl sodium salt

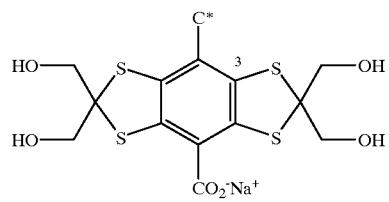

Tris(8-ethoxycarbonyl-2,2,6,6-tetrahydroxymethylbenzo[1,2-d:4,5-d']bis(1,3)dithiole-4-yl)methanol (3.4 mg, 0.0026 mmol) was dissolved in acetonitrile (2 ml) and the solution was cooled to 0° C. Trifluoromethane-sulfonic acid (0.017 ml) was added and after 15 min, a solution of $SnCl_2$ (0.4 mg) in acetonitrile (1 ml) was added. After another 15 min, an aqueous $NaH_2PO_4$ buffer was added and the solvents were removed by evaporation. The residue was suspended in water and the pH was adjusted to 12 using an 1M aqueous NaOH solution. After stirring for 1 h, the solution was neutralized with 1M aqueous HCl and the solvent was removed by evaporation. The product was purified by preparative HPLC. Yield: 2.0 mg (60%).

ESR (1.5 mM in $H_2O$, 100 G): singlet, linewidth 100 mG.

This compound is also useful in the method of the invention.

Example 15

2,2,6,6-Tetramethylbenzo[1,2-d:4,5-d']-bis(1,3)dioxole-4-carboxylic acid

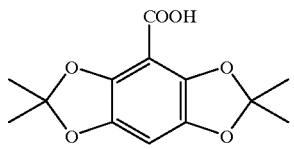

2,2,6,6-Tetramethylbenzo[1,2-d:4,5-d']-bis(1,3)dioxole (10.0 g, 45.0 mmol; prepared according to WO-91/12024)

was dissolved in dry THF (200 mL) under an argon atmosphere. The solution was cooled to −20° C. and n-butyllithium (20.0 mL, 50.0 mmol) in hexane was added. After attaining ambient temperature, the reaction mixture was transferred onto solid carbon dioxide (150 g) and allowed to stand overnight. Water (200 mL) was added and pH was adjusted to 10 using 2M aqueous NaOH. After washing with ether, the aqueous phase was acidified with 2M hydrochloric acid to pH 2 and extracted with ether (2*300 mL). The organic phases were dried ($Na_2SO_4$) and evaporated to give the pure product.

Yield: 10.7 g (89%).

1H NMR (CDCl3, 300 MHz) δ: 6.50 (s, 1H), 1.71 (s, 12H).

$^{13}$C NMR ($CDCl_3$, 75 MHz) δ: 165.1, 140.9, 140.8, 119.8, 98.9, 97.3, 25.6.

Example 16
2,2,6,6-Tetramethylbenzo[1,2-d:4,5-d']-bis(1,3)dioxole-4-carboxylic acid methyl ester

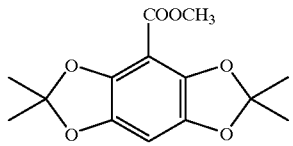

2,2,6,6-Tetramethylbenzo[1,2-d:4,5-d']-bis(1,3)dioxole-4-carboxylic acid (10.0 g, 38.0 mmol) was dissolved in dry DMF (100 mL). Potassium carbonate (15.2 g, 110.0 mmol) was added and the reaction was heated to 55° C. for 30 min. After cooling to ambient temperature, methyl iodide (15.6 g, 110.0 mmol) was added and the solution was stirred overnight. The precipitate was filtered off and the solution was evaporated. The residue was dissolved in saturated aqueous $NaHCO_3$ and ether. The aqueous layer was discarded and the organic phase was dried ($Na_2SO_4$), filtered and evaporated to give 9.4 g (88%) of the pure product.

$^1$H NMR ($CDCl_3$, 300 MHz) δ: 6.44 (s, 1H), 3.85 (s, 3H), 1.65 (s, 12H).

$^{13}$C NMR ($CDCl_3$, 75 MHz) δ: 163.4, 140.8, 140.6, 119.0, 99.9, 99.4, 51.9, 25.6.

Example 17
Bis-(2,2,6,6-tetramethylbenzo[1,2-d:4,5-d']-bis(1,3)diyhiole-4-yl)-mono-(2 2,6,6-tetramethylbenzo[1,2-d:4,5-d']-bis(1,3)dioxole-4-yl)methanol

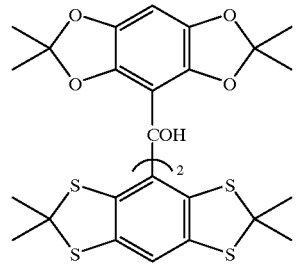

2,2,6,6-Tetramethylbenzo[1,2-d:4,5-d ']bis(1,3)dithiole (2.86 g, 10 mmol; prepared according to WO-91/12024) was dissolved in anhydrous THF (75 mL) and cooled to −70° C. n-Butyllithium (4.4 mL, 2.5M in hexane) was added. The reaction mixture was allowed to reach ambient temperature. 4-Methoxycarbonyl-2,2,6,6-tetramethylbenzo-[1,2-d:4,5-d']-bis-(1,3)-dioxole (1.4 g, 5 mmol) was added as a solid. After 1 hour, the mixture was quenched with saturated aqueous $NaH_2PO_4$. The aqueous phase was discarded and the organic layer evaporated. The residue was dissolved in dichloromethane, washed with water and dried ($Na_2SO_4$). The product was purified by column chromatography (dichloromethane:heptane, 1:1) giving 1.8 g (44%) of pure product.

$^1$H NMR ($CDCl_3$, 300 MHz) δ: 7.10 (broad s, 2 H, ArH), 6.39 (s, 1 H, ArH), 4.79 (s, 1 H, OH), 1.82–1.56 (m, 24 H, $CH_3$), 1.53 (s, 6 H, $CH_3$), 1.46 (s, 6 H, $CH_3$).

Example 18
Bis-(B-ethoxycarbonyl-2,2,6,6-tetramethylbenzo[1,2-d:4,5-d']-bis(1,3)dithiole-4-yl)-mono-(8-ethoxycarbonyl-2,2,6,6-tetramethylbenzo[1,2-d:4,5-d']-bis(1,3)dioxol-4-yl) methanol

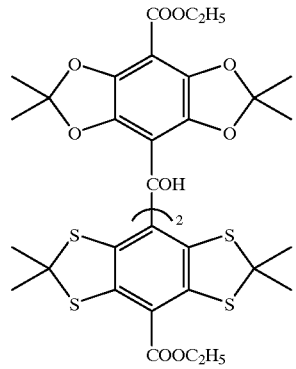

Bis-(2,2,6,6-tetramethylbenzo[1,2-d:4,5-d']-bis(1,3)dithiole-4-yl)-mono-(2,2,6,6-tetramethylbenzo[1, 2-d:4,5-d']-bis(1,3)dioxol-4-yl)methanol (0.50 g, 0.61 mmol) was dissolved in dry benzene (6.0 mL) under an atmosphere of argon. t-Butyllitium (2.44 mL, 1.5M in pentane) and TMEDA (0.545 mL, 3.66 mmol) were added. The reaction mixture was subjected to ultrasound for 25 min. and was then slowly added to a solution of diethyl carbonate (7.2 mL, 59.4 mmol) in dry benzene (16 mL). After stirring for 1.5 h, aqueous $NaH_2PO_4$(50 mL) was added. The organic layer was separated, washed with water, dried ($Na_2SO_4$) and evaporated. After purification by preparative HPLC 130.0 mg (21%)) of the pure product was obtained.

$^1$H NMR ($CDCl_3$, 300 MHz) δ: 4.98 (s, 1H), 4.28–4.37 (m, 6H) 1.48–1.79 (m, 36H), 1.46 (t, 6H, J 7.0 Hz), 1.38 (t, 3H, J 7.0 Hz).

$^{13}$C NMR ($CDCl_3$, 75 MHz) δ: 166.2, 166.0, 162.9, 141.9, 141.6, 141.2, 140.8, 140.4, 140.0, 136.6, 134.5, 129.9, 128.5, 128.1, 127.8, 127.2, 120.3, 118.9, 111.9, 101.1, 80.6, 62.1, 61.0, 60.3, 60.2, 59.8, 59.2, 34.4, 34.3, 33.5, 28.8, 28.1, 27.0, 26.9, 26.5, 25.8.

Example 19
Bis-(8-ethoxycarbonyl-2,2,6,6-tetramethylbenzo[1,2-d:4,5-d']-bis(1,3)dithiole-4-yl)-mono-(8-ethoxycarbonyl-2,2,6,6-tetramethylbenzo[1,2-d:4,5-d']-bis(1,3)dioxol-4-yl)methyl

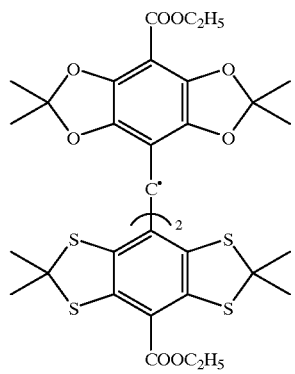

Bis-(8-ethoxycarbonyl-2,2,6,6-tetramethylbenzo[1,2-d:4,5-d']-bis(1,3)dithiol-4-yl)-mono-(8-ethoxycarbonyl-2,2,6,6-tetramethylbenzo[1,2-d:4,5-d']-bis(1,3)dioxol-4-yl) methanol (520 mg, 0.501 mmol) was dissolved in dry degassed dichloromethane (15 mL) together with tin(II) chloride (95 mg, 0.501 mmol) and acetonitrile (5 mL). $BF_3.Et_2O$ (70 μL, 0.557 mmol) was added and the solution was stirred for 20 min. After addition of dichloromethane (80 ML) and washing with degassed water (80 mL), the organic layer was separated, dried ($MgSO_4$), filtered and evaporated. The product was purified by preparative HPLC. Yield: 110 mg (22%).

ESR (THF, 200 G) singlet, line width 325 mG.

Overhauser enhancement (THF, 2.1 mM): !156 at 4 W microwave power.

Stability measurements: Half life in acetonitrile without exclusion or air: 2000 h.

Example 20

Bis-(8-potassium carboxylate-2,2,6,6-tetramethylbenzo[1,2-d:4 5-d']-bis(1,3)dithiol-4-yl)-mono-(8-potassium carboxylate-2,2,6,6-tetramethylbenzo[1,2-d:4,5-d']-bis (1,3) dioxol-4-yl)methyl

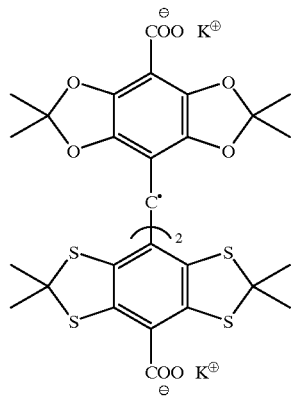

Bis-(8-ethoxycarbonyl-2,2,6,6-tetramethylbenzo[1,2-d:4,5-d']-bis(1,3)dithiol-4-yl)-mono-(8-ethoxycarbonyl-2,2,6,6-tetramethylbenzo[1,2-d:4,5-d']-bis(1,3)dioxol-4-yl)methyl (132 mg, 0.129 mmol) was dissolved in ethanol (10 mL). Aqueous potassium hydroxide (5 mL, 1.0M) was added and the reaction mixture was stirred at 50° C. overnight. After evaporation of the ethanol, the mixture was stirred for 1 h at 50° C. and was then acidified with 2M hydrochloric acid. The aqueous phase was extracted with ether. The organic phase was separated, dried ($MgSO_4$) filtered and evaporated. The product was purified by preparative HPLC. The fractions were evaporated and water was added. The aqueous layer was extracted with ether. The organic layer was separated, dried ($MgSO_4$), filtered and evaporated. The product was dissolved by adding water and 1M KOH (0.387 mL, 0.387 mmol). The solution was lyophilized.

Yield: 101 mg (75%).

ESR ($H_2O$, 200 G): singlet, line width 105 mG. Overhauser enhancement ($H_2O$, 6.9 mM): 219 at 0.012 W microwave power.

Example 21

Benzo[1,2-d:4,5-d']bis(1,3)dithiole-2,2,6,6-tetracarboxylic acid tetraethyl ester

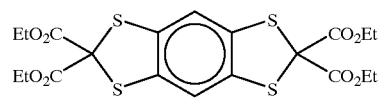

1,2,4,5-benzenetetrathiol (1.50 g, 7.28 mmol) was dissolved in dry DMF (55 ml) under an atmosphere of Argon and $K_2CO_3$ (4.0 g) was added together with 2,2-dibromomalonate ethyl ester (4.26 g, 14.6 mmol). The solution was stirred at room temperature for 16 h and then at 60° C. for an additional 5 h. The reaction mixture was then poured into an ice-water mixture (200 g–200 ml) and extracted with ethyl acetate (2×250 ml). The combined organic phases were washed with water (4×100 ml) dried ($Na_2SO_4$) and evaporated. The crude product was washed sufficiently pure to be used in the next step without purification. Yield: 3.05 g (80%) 1H NMR (300 MHz, $CDCl_3$): 6.91 (s,2H), 4.29 (q, J=7.2 Hz, 8H), 1.28 (t, J=7.2 Hz, 12H).

Example 22

2,2,6,6-tetra(hydroxymethyl-$d_2$)benzo[1,2-d:4,5-d']bis(1,3) dithiole

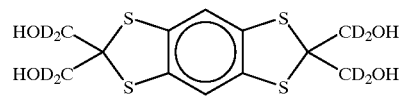

A dry Soxhlet setup was provided with Benzo[1,2-d:4,5-d']bis(1,3)dithiole-2,2,6,6-tetracarboxylic acid tetraethyl ester (5.0 g, 9.65 mmol) in the upper compartment and a mixture of lithium aluminium deuteride (1.62 g, 38.6 mmol) and diethyl ether (300 ml) in the lower, round-bottomed flask. The ether was heated to reflux temperature for 20 h and the mixture was then allowed to cool. Methanol (150 ml) was added dropwise by water (50 ml). The mixture was acidified with concentrated HCl (20 ml) and the solvent was reduced to 50 ml by evaporation in vacuum. The white solid was filtered off, washed with water (2×25 ml) and dried. Yield 3.15 g (91%).

1NMR (300 MHz, DMSO-$d_6$): 7.06 (2,2H), 5.45 (br s, 4H)

Example 23
2,2,6,6-Tetra(dimetylthexylsilyloxymethyl)benzo[1,2-d:4,5-d']bis(1,3)dithiole

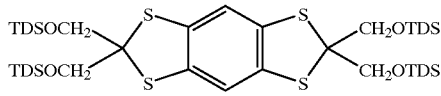

The reaction was performed under argon atmosphere. 2,2,6,6-Tetra(hydroxymethyl)benzo[1,2-d:4,5-d']bis(1,3)dithiole (0.8 g, 2.2 mmol) was dissolved in DMF (20 mL). Imidazole (1.1 g, 15.8 mmol) was added and the solution was cooled to 0° C. Dimethylthexylsilyl chloride (2.8 g, 15.8 mmol) was added dropwise (ca 2 min). The solution was stirred for 48 hours at ambient temperature. The reaction mixture was poured into ice/water, $CH_2Cl_2$(100 mL) was added and the two phases were separated. The organic phase was washed with 1M HCl and water (3*100 mL). The solution was dried ($Na_2SO_4$) and evaporated. The product was purified by column chromatography using dichloromethane-heptane (1:9) as eluent.

Yield: 1.1 g (52%)

$^1$H NMR (CDCl$_3$, 300 MHz) δ: 6.84 (s, 2H, ArH), 3.94 (s, 8H, CH$_2$), 1.62 (septet, 4H, J 6.8 Hz, CH), 0.88 (d, 24H, J 6.8 Hz, CH$_3$), 0.84 (s, 24H, CH$_3$), 0.08 (s, 24H, Si(CH$_3$)$_2$).

$^{13}$C NMR (CDCl$_3$, 75 MHz) δ: 134.3, 115.8, 74.2, 65.0, 34.2, 25.1, 20.3, 18.6, −3.6.

Example 24
Bis(2,2,6,6-tetra(dimetylthexylsilyloxymethyl)benzo[1,2-d:4,5-d']bis(1,3)dithiol-4-yl)-mono(2,2,6,6-tetramethylbenzo[1,2-d:4,5-d']-bis(1,3)dioxol-4-yl))methanol

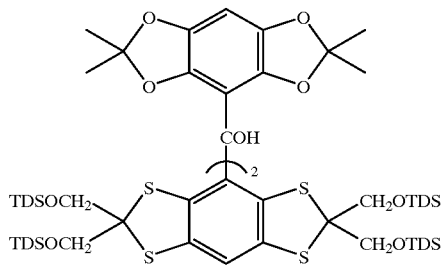

The reaction was performed under argon atmosphere. 2,2,6,6-Tetra(dimetylthexylsilyloxymethyl)benzo[1,2-d:4,5-d']bis(1,3)dithiole (7.0 g, 7.6 mmol) was dissolved in dry THF (50 mL). The solution was cooled to −70° C. n-Butyllithium (5.0 mL, 1.6M in hexane) was added and the temperature was allowed to attain ambient temperature and was stirred for 1 h. The solvent was evaporated in vacuum at ambient temperature and diethyl ether (20 mL) was added. Then, 4-ethoxycarbonyl-2,2,6,6-tetramethylbenzo[1,2-d:4,5-d']-bis(1,3)dioxole (0.8 g, 2.9 mmol) was added in one portion and the reaction mixture was stirred at ambient temperature for 12 h. The mixture was poured into a NaH$_2$PO$_4$ solution, the phases were separated and the aqueous phase was extracted with diethyl ether (2*100 mL). The organic phases were dried (Na$_2$SO$_4$) and evaporated. The residue was purified by preparative HPLC.

Yield: 3.7 g (62%).

$^1$H NMR (CDCl$_3$, 300 MHz) δ: 6.80 (s, 2H, ArH), 6.26 (s, 1H, ArH), 4.95 (s, 1H, OH), 3.8 (br m, 16H, CH$_2$), 1.5 (br m, 20H, CH$_3$+CH), 0.9 (d, 48H, CH$_3$), 0.7 (s, 48H, CH$_3$), 0.2 (2 s, 48H, Si(CH3)$_2$).

$^{13}$C NMR (CDCl$_3$, 75 MHz) δ: 141.5, 140.3, 139.8, 139.6, 131.7, 118.6, 117.1, 108.1, 94.4, 80.0, 65.4, 34.1, 25.9, 25.0, 20.3, 18.7, −3.2.

Example 25
Bis(8-ethoxycarbonyl-2,2,6,6-tetra(hydroxymethyl)benzo[1,2-d:4,5-d']bis(1,3)dithiol-4-yl)-mono(8-ethoxycarbonyl-2,2,6,6-tetramethylbenzo[1,2-d:4,5-d']-bis(1,3)dioxol-4-yl))methanol

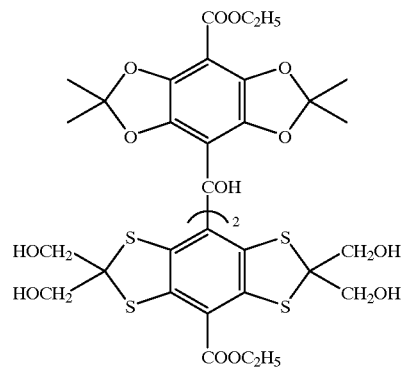

Bis(2,2,6,6-tetra(dimetylthexylsilyloxymethyl)benzo[1,2-d:4,5-d']bis(1,3)dithiol-4-yl)-mono(2,2,6,6-tetramethylbenzo[1,2-d:4,5-d']-bis(1,3)dioxol-4-yl))methanol (3.2 g, 1.54 mmol) was dissolved in heptane (12.8 mL) and dry benzene (10.7 mL) together with TMEDA (3.2 mL, 21.6 mmol) under an atmosphere of argon. The solution was cooled to −22° C. and t-BuLi (14.4 mL, 1.5M in pentane) was added. After stirring for 3 h at −22° C., the reaction mixture was transferred into a solution of diethyl pyrocarbonate (12.8 mL, 87 mmol) in heptane (23 mL) and dry benzene (23 mL) which was kept at −22° C. The reaction mixture was then allowed to attain ambient temperature. After stirring for an additional hour, a saturated aqueous solution of NaH$_2$PO$_4$ (40 mL) was added. The mixture was stirred for one hour, the organic phase was separated, washed with water (2*100 mL) and acetonitrile (2*100 mL). The heptane/benzene phase was evaporated and then dissolved in THF (25 mL) A solution of Bu$_4$NF in THF (20 mL, 20 mmol) was added and the mixture was stirred overnight. After evaporation of the solvent, the residue was partitioned between water (300 mL) and ethyl acetate (300 mL). The organic phase was washed with water (2*100 mL), dried (Na$_2$SO$_4$) and evaporated. Purification by preparative HPLC gave 400 mg (22%) pure product.

$^1$H NMR (CDCl$_3$, 300 MHz) δ: 5.78–5.92 (m, 6H), 5.03–5.52 (m, 24H), 2.98–3.21 (m, 12H), 2.90 (t, 6H, J 7.0 Hz), 2.84 (t, 3H, J 6.9 Hz).

Example 26
Bis(8-ethoxycarbonyl-2,2,6,6-tetra(hydroxymethyl)benzo[1,2-d:4,5-d']bis(1,3)dithiol-4-yl)-mono(8-ethoxycarbonyl-2,2,6,6-tetramethylbenzo[1,2-d:4,5-d']-bis(1,3)dioxol-4-yl))methyl

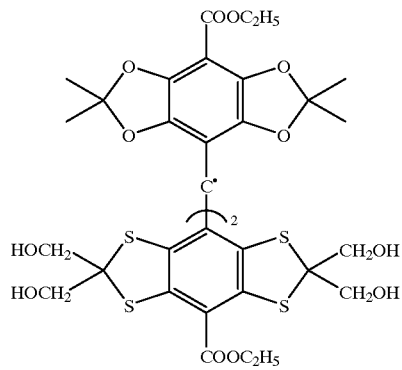

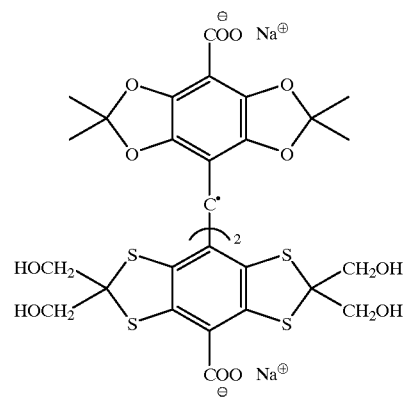

Bis(8-ethoxycarbonyl-2,2,6,6-tetra(hydroxymethyl)benzo[1,2-d:4,5-d']bis(1,3)dithiol-4-yl)-mono(8-ethoxycarbonyl-2,2,6,6-tetramethylbenzo[1,2-d:4,5-d']-bis(1,3)dioxol-4-yl))methanol (294 mg, 0.25 mmol) was dissolved in acetonitrile (70 mL) under an atmosphere of argon. After cooling to 0° C., trifluoromethane sulfonic acid (190 µL, 2.2 mmol) was added. After stirring for 3 min, tin(II) chloride (48 mg, 0.25 mmol) dissolved in acetonitrile (7 mL) was added. After 1 min, a saturated aqueous solution of $NaH_2PO_4$ (50 mL) was added. The aqueous phase was washed with acetonitrile (2*50 mL), the combined organic phases were dried ($Na_2SO_4$) and evaporated. Purification by preparative HPLC gave 176 mg (61%) of the pure product.

ESR ($H_2O$, 200 G): singlet, linewidth 433 mG.

Example 27

Bis(8-carboxy-2,2,6,6-tetra(hydroxymethyl)benzo[2-d:4,5-d']bis(1,3)dithiol-4-yl)-mono(8-carboxy-2,2,6,6-tetramethylbenzo[2-d:4,5-d']-bis(1,3)dioxol-4-yl)) methyl sodium salt Bis(8-ethoxycarbonyl-2,2,6,6-tetra(hydroxymethyl)benzo[1,2-d:4,5-d']bis(1,3)dithiol-4-yl)-mono(8-ethoxycarbonyl-2,2,6,6-tetramethylbenzo[2-d:4,5-d']-bis(1,3)dioxol-4-yl))methyl (316 mg, 0.275 mmol) was dissolved in a mixture of 1M aqueous NaOH (3 mL), water (1.5 mL) and ethanol (3 mL). The solution was stirred at ambient temperature for 15 min, the ethanol was removed by evaporation, and the residue was stirred at ambient temperature for additional 2 hours. After evaporation to near dryness, the pure acid (240 mg, 82%) was isolated by preparative HPLC followed by lyophilization. The acid was converted into the corresponding sodium salt by the addition of water (50 mL) followed by adjustment of the pH to 7 with 1M aqueous NaOH and lyophilization.

ESR (3.4 mM in $H_2O$, 200 G): singlet, linewidth 120 mG.

Overhauser enhancement (aqueous solution as above): 164 at 5 W microwave power.

Stability measurements: Half life in water without exclusion of air: 120 h.

Example 28

A schematic representation of the "elementary method" according to the invention using the perdeuterated hydroxy trityl. The self- and oxygen broadening is given by eq. 1, the inhomogeneous broadening is $\Delta H_{PP}^{G}$=60 mG and the relaxivity 0.4 $mM^{-1}s^{-1}$. Images A, B and C:

$P = P_A$  $P = P_B$  $P = P_C$
$\Delta H = 0$  $\Delta H = 0$  $\Delta H = 150$ m on a pixel-by-pixel basis $$I_A = A\left\{0.4\,mM^{-1}s^{-1}c_{rad}\left\{1-\sqrt{\frac{2}{\pi}}\frac{1}{90\,mG}\int_{-\infty}^{\infty}\exp(-2H'^2/(60\,mG)^2)\frac{1+\frac{4}{3}H'^2/\Delta H_{pp}^{L2}}{1+\frac{4}{3}H'^2/\Delta H_{pp}^{L2}+\frac{2}{\sqrt{3}}\alpha P_A\gamma_e T_{1e}/\Delta H_{pp}^{L}}dH'\right\}-1\right\}$$

$$I_B = A\left\{0.4\,mM^{-1}s^{-1}c_{rad}\left\{1-\sqrt{\frac{2}{\pi}}\frac{1}{90\,mG}\int_{-\infty}^{\infty}\exp\{-2H'^2/(60\,mG)^2\}\frac{1+\frac{4}{3}H'^2/\Delta H_{pp}^{L2}}{1+\frac{4}{3}H'^2/\Delta H_{pp}^{L2}+\frac{2}{\sqrt{3}}\alpha P_B\gamma_e T_{1e}/\Delta H_{pp}^{L}}dH'\right\}-1\right\}$$

$$I_C = A\times\left\{0.4\,mM^{-1}s^{-1}c_{rad}\left\{1-\sqrt{\frac{2}{\pi}}\frac{1}{90\,mG}\int_{-\infty}^{\infty}\exp\{-2H'^2/(60\,mG)^2\}\frac{1+\frac{4}{3}(\Delta H-H')^2/\Delta H_{pp}^{L2}}{1+\frac{4}{3}(\Delta H-H')^2/\Delta H_{pp}^{L2}+\frac{2}{\sqrt{3}}\alpha P_C\gamma_e T_{1e}/\Delta H_{pp}^{L}}dH'\right\}-1\right\}$$

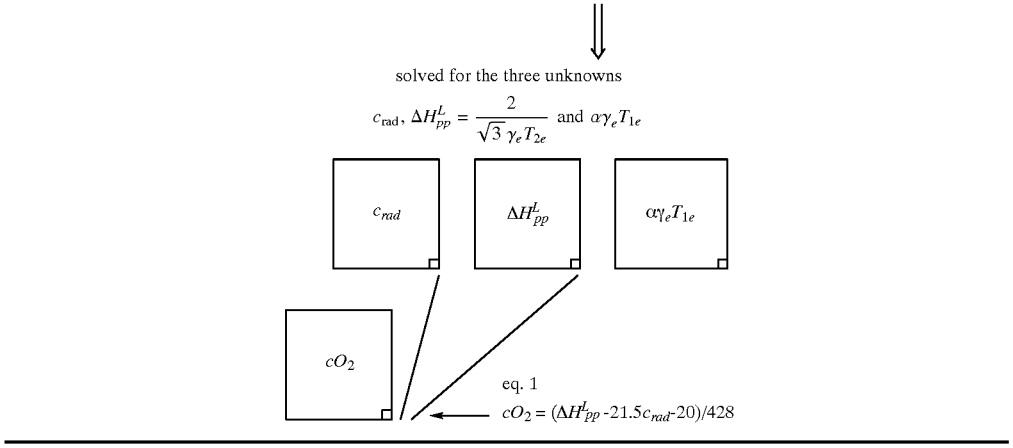
Example 29
A schematic representation of the preferred method according to the invention using the perdeuterated hydroxy trityl. The self- and oxygen broadening is given by eq. 1, the inhomogeneous broadening is $\Delta H_{PP}^G = 60$ mG and the relaxivity 0.4 mM$^{-1}$s$^{-1}$. Images A,B,C,D and E:
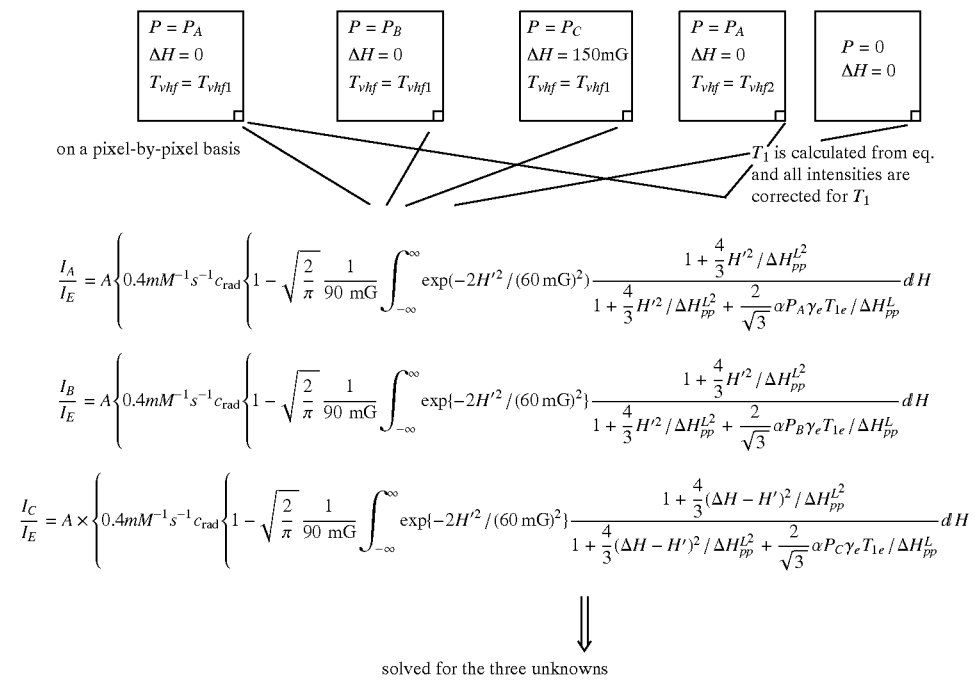

-continued

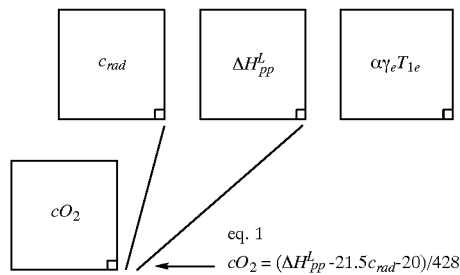

eq. 1
$cO_2 = (\Delta H^L_{pp} - 21.5 c_{rad} - 20)/428$

What is claimed is:

1. A method of determining oxygen concentration in a sample, said method comprising the following steps: introducing into said sample an effective amount of a physiologically tolerable free radical having an esr transition with a linewidth measured in water of less than 400 mG; irradiating said sample with radiation of an amplitude and frequency selected to stimulate an electron spin resonance transition of said radical; detecting electron spin resonance enhanced magnetic resonance signals from said sample under at least first, second and third conditions, wherein under said first and second conditions said radiation is of a first frequency, under said third conditions said radiation is of a second frequency different from said first frequency, under said first, second and third conditions said radiation is of a first, second and third amplitude, said first and second amplitudes at least being different from each other; and manipulating said detected signals to determine oxygen concentration in said sample.

2. A method as claimed in claim 1 wherein the step of manipulating said detected signals comprises generating an image data set.

3. A method as claimed in claim 2 comprising
   (a) generating a first OMRI image of said sample at VHF power $P_A$, irradiation period $T_{VHF1}$ and on-resonance ($\Delta H = 0$),
   (b) generating a second OMRI image of said sample at a second VHF power $P_B$, irradiation time $T_{VHF1}$ and on-resonance ($\Delta H = 0$)
   (c) generating a third OMRI image of said sample at VHF power $P_C$, irradiation period $T_{VHF1}$ and off-resonance ($\Delta H \neq 0$)
   (d) manipulating the images obtained in steps (a) to (c) and calibrating using parameters determined ex vivo to provide an oxygen image of said sample.

4. A method as claimed in claim 3 wherein additionally a fourth image is generated at VHF power $P_A$ and irradiation period $T_{VHF2}$ and a fifth MR image is generated without VHF irradiation.

5. A method as claimed in claim 1 comprising the additional step of generating a native MR image of the sample.

6. A method as claimed in claim 1 in which the step of manipulating said detected signals comprises fitting the measured degree of saturation of the esr transition to a Voigtian function.

7. A method as claimed in claim 1 wherein said physiologically tolerable free radical is a radical which distributes into the extracellular fluid.

8. A method as claimed in claim 1 wherein said physiologically tolerable free radical has an esr transition with a linewidth measured in water of less than 150 mG.

9. A method as claimed in claim 8 wherein said radical has an esr transition with a linewidth of less than 60 mG.

10. A method as claimed in claim 1 wherein said physiologically tolerable free radical is a trityl.

11. A method as claimed in claim 10 wherein said trityl is of formula

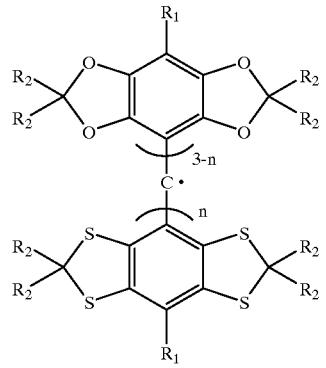

wherein:

n is 0, 1, 2 or 3;

$R^1$ is a carboxyl group or a derivative thereof;

$R^2$ is an optionally hydroxylated $C_{1-6}$-alkyl group; preferably a $C^nH_3$ or $C^nH_2OH$ group (where n is 1 or 2 i.e. $^2H$ is deuterium);

and the salts and precursors and deuterated analogs thereof.

12. A method as claimed in claim 10 wherein said trityl is of formula:

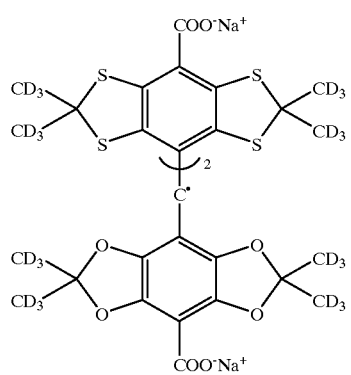

-continued

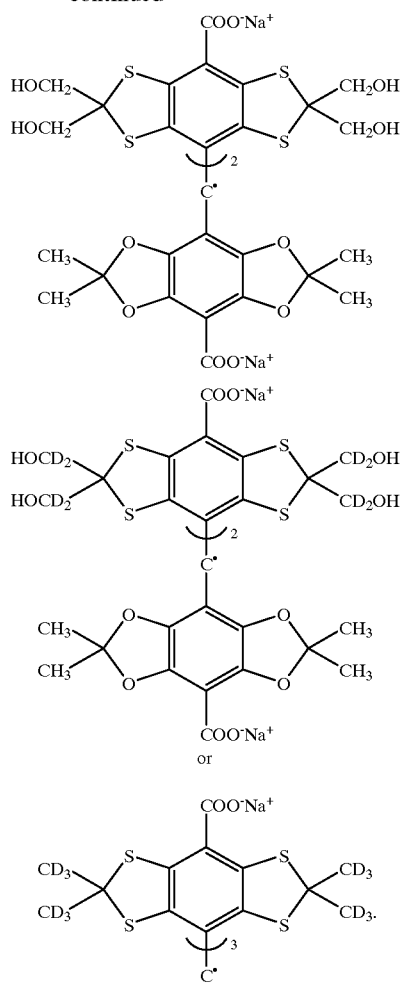

13. The method as claimed in claim 1, wherein manipulating said detected signals includes calibrating using parameters determined ex vivo.

14. The method as claimed in claim 13, wherein said parameters are determined under substantially the same conditions existing in the sample whose oxygen concentration is to be determined.

15. The method as claimed in claim 14, wherein said parameters are determined for a range of oxygen and radical concentrations in a fluid sample which corresponds to the fluid in which oxygenation is to be determined, at the same temperature as the temperature of the fluid in which oxygenation is to be determined.

16. The method as claimed in claim 14, wherein said parameters are determined in blood or a biological fluid corresponding to the fluid in which oxygenation is to be determined.

17. The method as claimed in claim 14, wherein said parameters are determined at 37° C.

18. The method as claimed in claim 13, wherein said parameters are determined under anaerobic conditions.

19. The method as claimed in claim 13, wherein said parameters are determined at an oxygen partial pressure of 100 mmHg.

20. The method as claimed in claim 13, wherein said parameters are determined for a range of oxygen concentrations up to a concentration of 0.5 mM.

21. The method as claimed in claim 20, wherein said parameters are determined for a range of oxygen concentrations up to a concentration of 0.1 mM.

22. The method as claimed in claim 13, wherein said parameters are determined for a range of radical concentrations up to a concentration of 1.5 mM.

23. The method as claimed in claim 22, wherein said parameters are determined for a range of radical concentrations up to a concentration of 1.0 mM.

24. The method as claimed in claim 22, wherein said parameters are determined for a range of radical concentrations up to a concentration of 0.2 mM.

* * * * *